US010136818B2

(12) United States Patent
Konen et al.

(10) Patent No.: US 10,136,818 B2
(45) Date of Patent: Nov. 27, 2018

(54) HIGH RESOLUTION INTRAOPERATIVE MRI IMAGES

(71) Applicants: Tel Hashomer Medical Research, Infrastructure and Services Ltd., Ramat Gan (IL); Ramot at Tel Aviv University Ltd., Tel Aviv (IL)

(72) Inventors: Eli Konen, Tel Aviv (IL); Arnaldo Mayer, Ramat Hasharon (IL); Moshe Hadani, Ramat Gan (IL); Nahum Kiryati, Tel Aviv (IL); Ori Weber, Tel Aviv (IL)

(73) Assignees: Tel Hashomer Medical Research, Infrastructure and Services Ltd., Ramat Gan (IL); Ramot at Tel Aviv University Ltd., Tel Aviv (IL)

( * ) Notice: Subject to any disclaimer, the term of this patent is extended or adjusted under 35 U.S.C. 154(b) by 40 days.

(21) Appl. No.: 15/307,012

(22) PCT Filed: Apr. 28, 2015

(86) PCT No.: PCT/IB2015/053090
§ 371 (c)(1),
(2) Date: Oct. 27, 2016

(87) PCT Pub. No.: WO2015/166413
PCT Pub. Date: Nov. 5, 2015

(65) Prior Publication Data
US 2017/0046826 A1 Feb. 16, 2017

Related U.S. Application Data

(60) Provisional application No. 61/984,988, filed on Apr. 28, 2014.

(51) Int. Cl.
G06K 9/00 (2006.01)
A61B 5/00 (2006.01)
(Continued)

(52) U.S. Cl.
CPC ........ *A61B 5/0042* (2013.01); *G01R 33/4835* (2013.01); *G01R 33/5608* (2013.01);
(Continued)

(58) Field of Classification Search
CPC .................. G06T 7/003; G06T 3/4053; G06T 2207/10088; G06T 2207/30016; G01R 33/5608; G01R 33/4835; A61B 5/0042
See application file for complete search history.

(56) References Cited

U.S. PATENT DOCUMENTS 5,245,282 A * 9/1993 Mugler, III ........ G01R 33/4835
324/309
6,426,994 B1 * 7/2002 Van Vaals .............. G01R 33/56
378/98.12
(Continued)

OTHER PUBLICATIONS

International Search Report dated Oct. 6, 2015 for International Application No. PCT/IB15/53090 filed Apr. 28, 2015.
(Continued)

*Primary Examiner* — Amir Alavi
(74) *Attorney, Agent, or Firm* — A. C. Entis-IP Ltd.; Allan C. Entis

(57) ABSTRACT

A method of providing an intraoperative magnetic resonance image of a target site of a patient body at which a medical procedure is performed comprising determining a rigid body transform that transforms a high resolution preoperative magnetic resonance image, $MRI_o$, of the target site to a preoperative magnetic resonance image, $iMRI_o$, of the target site acquired by an interoperative iMRI scanner, and a non-rigid body transform that transforms the $iMRI_o$ image to an image $iMRI_1$ image of the site acquired by the interoperative iMRI scanner during the medical procedure, and using the rigid and non-rigid body transforms to transform the high resolution $MRI_o$ image.

19 Claims, 11 Drawing Sheets

(51) Int. Cl.
  *G01R 33/56* (2006.01)
  *G06T 3/00* (2006.01)
  *G06T 7/30* (2017.01)
  *G01R 33/483* (2006.01)
  *G06T 3/40* (2006.01)
  *G06T 7/00* (2017.01)

(52) U.S. Cl.
  CPC .......... *G06T 3/0068* (2013.01); *G06T 3/4053* (2013.01); *G06T 7/003* (2013.01); *G06T 7/30* (2017.01); *G06T 2207/10088* (2013.01); *G06T 2207/20016* (2013.01); *G06T 2207/30016* (2013.01)

(56) References Cited

U.S. PATENT DOCUMENTS

| | | | | |
|---|---|---|---|---|
| 6,479,996 | B1* | 11/2002 | Hoogeveen | G01R 33/4835 324/307 |
| 9,619,904 | B2* | 4/2017 | Weizman | G06T 11/003 |
| 9,659,368 | B2* | 5/2017 | Alsop | G06T 7/0012 |
| 2003/0233039 | A1 | 12/2003 | Shao et al. | |
| 2005/0245810 | A1* | 11/2005 | Khamene | G01R 33/56 600/410 |
| 2006/0002630 | A1 | 1/2006 | Fu et al. | |
| 2007/0276234 | A1 | 11/2007 | Shahidi | |
| 2010/0217109 | A1* | 8/2010 | Belcher | A61B 5/055 600/410 |
| 2012/0155734 | A1 | 6/2012 | Barratt et al. | |
| 2013/0006095 | A1 | 1/2013 | Jenkins et al. | |
| 2014/0180060 | A1* | 6/2014 | Parrish | G01R 33/4806 600/411 |
| 2015/0018666 | A1* | 1/2015 | Madabhushi | A61B 8/12 600/411 |
| 2015/0250450 | A1* | 9/2015 | Thomas | A61B 8/4416 600/411 |
| 2017/0046826 | A1* | 2/2017 | Konen | G01R 33/5608 |

OTHER PUBLICATIONS

Ignacio Arganda-Carreras et al., Consistent and Elastic Registration of Histological Sections using Vector-Spline Regularization.

John Ashburner et al., Voxel-Based Morphometry—The Methods, NeuroImage 11, (2000), pp. 805-821.

Jian Chen et al., Real-time multi-modal rigid registration based on a novel symmetric-SIFT descriptor, Progress in Natural Science 19 (2009), pp. 643-651.

Moshe Hadani, Development and Design of Low Field Compact Intraoperative MRI for Standard Operating Room, pp. 29-32.

Arno Klein et al., Evaluation of 14 nonlinear deformation algorithms applied to human brain MRI registration, NeuroImage (2009), pp. 1-17.

Emma B. Lewis et al., Correction of differential intensity inhomogeneity in longitudinal MR images, NeuroImage 23 (2004), pp. 75-83.

Josien P. W. Pluim et al., Mutual information based registration of medical images: a survey, IEEE Transactions on Medical Imaging 2003, pp. 1-21.

Stephen M. Smith, Fast Robust Automated Brain Extraction, Human Brain Mapping 17, (2002), pp. 143-155.

Su Wang Lihong Li et al., Multiplicative versus Additive Bias Field Models for Unified Partial-Volume Segmentation and Inhomogeneity Correction in Brain MR Images, IEEE Nuclear Science Symposium Conference Record, 2008, pp. 4976-4982.

Guorong Wu et al., S-HAMMER: Hierarchical Attribute-Guided, Symmetric Diffeomorphic Registration for MR Brain Images, Hum Brain Mapp. Mar. 2014; 35(3), pp. 1044-1060.

European Partial Search Report dated Nov. 14, 2017 for European Application No. 15786028.9 filed Nov. 22, 2016.

Clatz O Et al., Robust Nonrigid Registration to Capture Brain Shift From Intraoperative MRI. IEEE Transactions on Medical Imaging, IEEE Service Center, Piscataway, NJ, US, vol. 24 No. 11, Nov. 1, 2005, pp. 1417-1427.

Archip N Er al., Non-rigid Alignment of Preoperative MRI. FMRI and DT-MRI with Intraoperative MRI to enhance visualization and navigation in image-guided neurosurgery, Journal of Biomechanics, Pergamon Press, New York, NY, US, vol. 39 Jan. 1, 2006, p. S574.

* cited by examiner

HIGH RESOLUTION INTRAOPERATIVE MRI IMAGES

RELATED APPLICATIONS

The present application is a U.S. National Phase Application of PCT/IB2015/053090 filed on Apr. 28, 2015, which claims the benefit under 35 U.S.C. § 119(e) of U.S. Provisional Patent Application 61/984,988 filed on Apr. 28, 2014, the disclosure of which is incorporated herein by reference.

TECHNICAL FIELD

Embodiments of the disclosure relate to intraoperative MRI images of a target site at which a medical procedure is performed

BACKGROUND

Magnetic resonance imaging (MRI) is an imaging modality that is typically used to acquire images of internal features in a region of interest (ROI) of a person's body, and many and different MRI techniques have been developed to tailor MRI imaging to imaging different internal structures of the body. Modern MRI scanners used to acquire the MRI images may typically be configured to provide MRI images of internal features in an ROI of the body having spatial resolution as fine as 1 $mm^3$ (cubic millimeter), and MRI scanners with microscopic resolution are available that resolve structural details of animal tissue as small as 0.1 $mm^3$.

To acquire an MRI image of an ROI of a person's body, the person is placed in a relatively strong, uniform "polarizing magnetic field" to align spins of atoms in the person's body having magnetic moments along a same axis, conventionally referred to as a z-axis. A pulse of radio frequency (RF) energy is transmitted to illuminate the ROI and tilt the magnetic moments and thereby the spins of atoms in a thin slice of the ROI away from the z-axis by a predetermined tilt angle, generally equal to about 90°. Following "tilting", conventionally referred to as "flipping", by the RF pulse, the ROI is exposed to a perturbing magnetic field, which is also directed along the z-axis but is configured to have a desired time dependent spatial gradient along orthogonal x and y axes that are perpendicular to the z-axis. The superposition of the perturbing magnetic gradient field and the polarizing magnetic field creates a time dependent "composite" magnetic field in the slice that is a function of spatial coordinates along the x and y axes. The flipped atoms precess around the z-axis with Larmor frequencies that are proportional to the magnitude of the composite magnetic field at the x and y coordinates in the slice at which they are located and radiate RF signals, hereinafter also referred to as MRI signals, at the Larmor frequencies at which they precess. The MRI signals from the atoms at a given x-y location in the slice have intensities that are proportional to the concentration of the radiating atoms at the location and are received by an RF receiving antenna.

The received RF signals provide a discrete Fourier transform of the spatial concentration of the radiating atoms in the slice which is inverse Fourier transformed to provide a spatial concentration of the flipped atoms as a function of their spatial coordinates, x, y, and z. The spatial concentration provides an image of cross sections of organs and features of the body that are transected by the slice. A sequence of MRI images of adjacent, parallel slices in the ROI along the z-axis is acquired and processed to produce three dimensional (3D) images of organs and features in the ROI. Generally, resolution and signal to noise ratio (SNR) of the images improve with magnitude and uniformity of the polarizing magnetic field. High resolution MRI scanners may generate polarizing magnetic fields having magnitudes from about 3 Tesla to about 5 Tesla To provide the strong polarizing magnetic field and the gradient magnetic field, a standard MRI scanner typically comprises a large tube or donut shaped housing that houses superconducting coils, which are excited to produce the polarizing magnetic field. Various additional current carrying coils that are excited to generate the gradient magnetic field are also housed in the housing.

The housing has a bore sufficiently large for receiving a human body, and during acquisition of MRI images of an ROI in a person's body completely surrounds the ROI. Typical standard MRI scanners therefore do not generally enable convenient access by a medical practitioner to perform a medical procedure, such as a surgery, at a target site of a patient's body while the target site is being imaged by the MRI scanner. As a result, whereas standard MRI scanners are often, and often indispensably, used to acquire high resolution images of a target site of a person's body in preparation for a medical procedure, the scanners are generally not readily used to acquire real time MRI images of the region during the procedure to track and update changes caused by the procedure. Often when used during a medical procedure, a patient is intermittently inserted and removed from the bore of a conventional MRI scanner to track progress of the procedure.

MRI scanners and MRI procedures referred to as intraoperative MRI (iMRI) scanners and interoperative iMRI procedures have been developed to improve usability of MRI imaging during medical procedures. The iMRI scanners and iMRI procedures may provide substantially real time MRI images of a target site during a medical procedure performed at the target site. Typically, an iMRI scanner generates polarizing magnetic fields having relatively small magnitudes, which may for example be as low as 0.15 to 0.5 Tesla, To enable advantageous physical access to a target site, the iMRI scanner may comprise a split housing comprising two donut shaped component housings that have relatively short bores and are placed facing each other on opposite sides of an access space. The component housings comprise superconducting coils that are excitable to generate a polarizing magnetic field in the access space. A patient may be placed in the iMRI scanner with a target site of the patient's body located in the access space so that a medical practitioner may have at least partial physical access to the target site to perform a medical procedure while the site is being imaged by the iMRI scanner to acquire mages for tracking and monitoring progress of the medical procedure.

Whereas an iMRI scanner may enable at least limited access to a target site of a person's body to perform an operation at the target site while the iMRI scanner images the target site, iMRI scanners, such as those developed for intraoperative MRI brain surgery often operate with low polarizing magnetic fields that are on the order of 0.15 Tesla and have a smaller field of view (FOV) than standard diagnostic MRI scanners. As a result, iMRI images that they provide generally have lower spatial resolution than standard diagnostic MRI images.

For example, prior to open brain surgery, relatively large FOV, high spatial resolution anatomical MRI, functional MRI (fMRI) and diffusion tensor MRI (DTI) images of the brain may be acquired using a standard high field MRI scanner to reference and direct navigation in the brain during surgery. The high resolution images may image the whole brain and skull and resolve features of the brain and skull having characteristic dimensions less than or equal to about a millimeter. After craniotomy to perform the surgery, it is generally impractical to acquire high resolution fMRI or DTI images, and an iMRI scanner may be used to acquire iMRI images of the brain during the surgery to aid in performing the surgery. However, because of a relatively small FOV of the iMRI scanner, the iMRI images may image only a part of the brain, and may have a slice thickness in a range from about 3 mm to about 5 mm, which is substantially thicker than that of the preoperative fMRI and DTI images. In addition, features of the brain imaged in the iMRI images may be deformed as a result of disturbance of the brain tissue by the surgery, making it difficult to accurately identify and locate the features during surgery. As a result, use of the iMRI images may be limited.

SUMMARY

An aspect of an embodiment of the disclosure relates to providing relatively high quality, high resolution intraoperative MRI images, hereinafter also referred to as "hiQ-iMRI" images, of a target site in a body at which an invasive medical procedure is being performed that are substantially contemporaneous with performance of the medical procedure. An aspect of an embodiment of the disclosure relates to providing a method for registering a relatively high resolution preoperative MRI image, hereinafter referred to as an "$MRI_o$" image, of the target site to iMRI images of the target site acquired during performance of the medical procedure to provide the hiQ-iMRI, images.

In accordance with an embodiment of the disclosure, a method of providing a hiQ-iMRI image of a target site during performance of the medical procedure at the target site comprises acquiring a high resolution preoperative $MRI_o$ image of the target site using a high resolution MRI scanner, and a preoperative MRI image, "$iMRI_o$" of the target site using an iMRI scanner. The $MRI_o$ image is registered to the $iMRI_o$ image using a rigid body registration algorithm to provide a rigid body transform "$iRT_o$" that transforms the $MRI_o$ image to the $iMRI_o$ image.

Following initiating the medical procedure and providing access to the target site, a first $iMRI_1$ image of the target site is acquired, optionally using the iMRI scanner that acquired the $iMRI_o$ image. Image $iMRI_1$ exhibits changes to tissue in the target site that may be generated by accessing the target site and initiating the medical procedure. A second rigid body transform $iRT_1$ that registers image $iMRI_o$ to image $iMRI_1$ may then be determined. A non-rigid registration transform, "$NRT_1$" may then be determined that operates to transform $iMRI_o$ after transformation by the rigid body transform $iRT_1$ to $iMRI_1$ to provide a first hiQ-$iMRI_1$ image of the target site, in accordance with an embodiment of the disclosure. In symbols, hiQ-$iMRI_1$=$NRT_1$·$iRT_1$·$iMRI_1$ where "·" represents operation of a transform, such as transform $iRT_1$, on an image, such as image $iMRI_1$, to transform the image. The non-rigid registration transform $NRT_1$ operates to appropriately morph $iRT_1$·$iMRI_1$ so that hiQ-$iMRI_1$ exhibits changes to tissue in the target site imaged in $iMRI_1$ that the medical procedure generated. In an embodiment of the disclosure, an additional "fine tuning" rigid body transform $iRT_{1*}$ and an additional "fine tuning" non-rigid body transform $NRT_{1*}$ are determined to register $iRT_o$·$MRI_o$ to $iMRI_1$. The additional transforms are applied to provide a fine tuned high quality image, hiQ-$iMRI_{1*}$, in accordance with a relationship hiQ-$iMRI_{1*}$= $NRT_{1*}$·$iRT_{1*}$·$NRT_1$·$iRT_1$·$iRT_o$·$MRI_o$=$NRT_{1*}$·$iRT_{1*}$·hiQ-$iMRI_1$ The hiQ-$iMRI_{1*}$ image of the target site therefore benefits from the high resolution of the $MRI_o$ image, and provides a substantially real time image of the shape and status of tissue in the target site at a time at which the $iMRI_1$ image of the target site is acquired. Subsequent high resolution intraoperative MRI images hiQ-$iMRI_{2*}$, hiQ-$iMRI_{3*}$, . . . during the medical procedure may be similarly generated in accordance with an embodiment of the disclosure by determining and using rigid and non-rigid transforms $iRT_2$, $NRT_2$, $iRT_{2*}$, $NRT_{2*}$, $iRT_3$, $NRT_3$, $iRT_{3*}$, $NRT_{3*}$, . . . responsive to intraoperative images $iMRI_2$, $iMRI_3$, . . . and preoperative image $MRI_o$.

In an embodiment of the disclosure the target site is a region of the brain and the medical procedure is an open brain surgery. $MRI_o$ image may comprise at last one, or any combination of more than one, of a contrast enhanced MRI image, anatomical T1 or T2 weighted image, an fMRI image, a DTI image, or a fluid attenuated inversion recovery (FLAIr) image. The $iMRI_o$ image comprises an MRI image acquired using an iMRI scanner prior to craniotomy and images $iMRI_1$, $iMRI_2$, $iMRI_3$, . . . are images acquired using the iMRI scanner during surgery following craniotomy.

There is therefore provided in accordance with an embodiment of the disclosure, a method of providing a high resolution intraoperative magnetic resonance imaging (hiQ-iMRI) image of a target site of a patient body at which a medical procedure is performed, the method comprising: acquiring a high resolution preoperative magnetic resonance image (MRI), $MRI_o$, of a first region of the patient comprising the target site, the $MRI_o$ image comprising a plurality of slices $MRI_{o,n}$ having voxels; acquiring a preoperative, $iMRI_o$ image of a second region of the patient comprising the target site, using an iMRI scanner having a field of view (FOV), the $iMRI_o$ image comprising a plurality of slices $iMRI_{o,m}$ having voxels; registering the $MRI_o$ image to the $iMRI_o$ image to provide a rigid body transform ($iRT_o$) that transforms the $MRI_o$ to the $iMRI_o$ image; acquiring an $iMRI_1$ image of the target site during performance of the medical procedure; registering the image $iMRI_o$ to the $iMRI_1$ image to obtain a non-rigid body transform (NRT); and applying $iRT_o$ and NRT to $MRI_o$ to provide a high resolution (hiQ-$iMRI_1$) image.

In an embodiment of the disclosure, the method comprises monitoring performance of the medical procedure responsive to the hiQ-$iMRI_1$. Additionally or alternatively, the method comprises directing performance of the medical procedure responsive to the hiQ-$iMRI_1$. Optionally, directing comprises controlling a surgery robot to perform the medical procedure.

There is further provided in accordance with an embodiment of the disclosure, a method of registering magnetic resonance imaging (MRI) images of a target site of a patient body at which a medical procedure is to be performed, the method comprising: acquiring a high resolution preoperative magnetic resonance image (MRI), $MRI_o$, of a first region of the patient comprising the target site, the $MRI_o$ image comprising a plurality of slices $MRI_{o,n}$ having voxels; acquiring a preoperative, $iMRI_o$ image of a second region of the patient comprising the target site, using an iMRI scanner having a field of view (FOV), the $iMRI_o$ image comprising plurality of slices $iMRI_{o,m}$ having voxels; determining whether a voxel in the $iMRI_o$ image is a marginal voxel located near an extremity of the FOV, and if the voxel is determined to be marginal; and registering the $MRI_o$ image to the iMRI$_o$ image to provide a rigid body transform (iRT$_o$) that transforms the MRI$_o$ to the iMRI$_o$ image, wherein registering is independent of the voxel if the voxel is determined to be marginal.

In an embodiment of the disclosure, registering the MRI$_o$ image to the iMRI$_o$ image comprises determining whether a voxel in the iMRI$_o$ image is a marginal voxel located near an extremity of the FOV, and if the voxel is determined to be marginal, registering the MRI$_o$ image to the iMRI$_o$ image independent of the voxel. Optionally, determining whether a voxel is marginal comprises determining an area of an intersection of a slice comprised in the iMRI$_o$ that contains the voxel with the FOV and determining that the voxel is marginal if the area of intersection is less than a threshold area. Optionally, the method comprises determining the threshold to be equal to a fraction less than one of a maximum intersection area of a slice of the plurality of slices in the iMRI$_o$ with the FOV. Optionally, the fraction is between about 0.5 and about 0.8.

In an embodiment of the disclosure, registering the MRI$_o$ image to the iMRI$_o$ image comprises segmenting tissue imaged in voxels comprised in slices of the plurality of slices in the iMRI$_o$ image to identify tissues in the iMRI$_o$ image. Optionally, the iMRI$_o$ image comprises voxels imaging a first tissue type located in the target site and voxels imaging a second tissue type located outside of the target site and comprising determining at least one connected region of voxels in the image iMRI$_o$ that are identified as candidates for imaging the second tissue type. Optionally, the first tissue comprises brain tissue and the second tissue comprises skull tissue. Additionally or alternatively, the method comprises performing a digital Radon transform of a connected region of the determined at least one connected region in each slice in which the connected region appears. Optionally, the method comprises determining that the connected region images a particular component of the patient responsive to at least one constraint that is a function of the Radon transform. Optionally, the at least one constraint comprises at least one constraint that is a function of a Radon angle, $\theta_M$, for which an average, $\overline{RM}(\theta_M)$, of maximum values of the Radon transform at each radon angle $\theta$ for slices of the plurality of slices of the iMRI$_o$, in which the connected region appears, is maximum. Optionally, the at least one constraint comprises at least one or any combination of more than one of a constraint on $\overline{RM}(\theta_M)$, $\overline{\rho}(\theta_M)$, and $\sigma(\theta_M)$, where $\overline{\rho}(\theta_M)$ is an average of Radon distances at Radon angle $\theta_M$ in slices of the plurality of slices in the iMRI$_o$ image in which the connected region appears and $\sigma(\theta_M)$, and is a standard deviation of $\overline{\rho}(\theta_M)$.

In an embodiment of the disclosure, the method comprises determining a cropping window for slices of the plurality of slices of the iMRI$_o$ image in which a connected region of the at least one connected region appears, the cropping window for any given slice including all of the at least one connected region that appears in the slice. Optionally, the cropping window is defined by a boundary comprising straight line segments. The boundary may be a polygon. The boundary may be a rectangle.

In an embodiment of the disclosure, the method comprises cropping slices of the plurality of slices for which a first cropping window is determined responsive to their respective cropping windows to generate a cropped iMRI$_o$ image. Optionally the method comprises positioning the cropping window associated with a slice comprised in iMRI$_o$ on a corresponding slice of the plurality of slices comprised in the MRI$_o$ image, and masking the corresponding slice to the cropping window to generate a masked MRI$_o$ image. Optionally the method comprises registering the masked MRI$_o$ image to the cropped iMRI$_o$ image to determine a rigid body transform RT(1)$_o$ between the MRI$_o$ image and the iMRI$_o$ image. Optionally the method comprises cropping slices of cropped slices in the cropped iMRI$_o$ image responsive to a boundary defined by the FOV to define an FOV cropped iMRI$_o$ image. Optionally the method comprises masking the MRI$_o$ image after masking the MRI$_o$ image to the cropping window and applying transform RT(1)$_o$ responsive to the boundary defined by the FOV to define an FOV masked MRI$_o$ image. Optionally the method comprises registering the FOV masked MRI$_o$ image to the FOV cropped iMRI$_o$ image to determine a rigid body transform RT(2)$_o$ between the MRI$_o$ image and the iMRI$_o$ image and a transform RT(2)$_o$·RT(1)$_o$, that transforms MRI$_o$ to iMRI$_o$. Optionally, the method comprises masking transformed image RT(2)$_o$·RT(1)$_o$·MRI$_o$ responsive to FOV and registering the masked image RT(2)$_o$·RT(1)$_o$·MRI$_o$ to FOV cropped image iMRI$_o$ to define a rigid transform RT(3)$_o$ that transforms RT(2)$_o$·RT(1)$_o$·MRI$_o$ to FOV cropped image iMRI$_o$. Optionally the method comprises iterating masking, transforming, and registering image MRI$_o$ to FOV cropped image iMRI$_o$ j times to define iRT$_o$=RT(j)$_o$ . . . RT(2)$_o$·RT(1)$_o$ where j is determined responsive to a criterion for ending the iteration.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

The following detailed description describes algorithms for providing hiQ-iMRI images, in accordance with embodiments of the disclosure. FIGS. 1A-1F provide a flow diagram of an algorithm in accordance with an embodiment of the disclosure which is applied, by way of example, to provide hiQ-MRI images for use in an open brain medical procedure. FIGS. 2A-5D show schematic images that provide visualizations of various stages noted in the flow diagram.

FIGS. 1A-1F show a flow diagram of an algorithm 20 for acquiring hiQ-iMRI images of a patient's brain for monitoring and directing navigation of an open brain medical procedure during the procedure. Optionally, the medical procedure is assumed to be a procedure for treating a lesion of the brain. Optionally, the lesion is assumed to be a tumor and the procedure a procedure for removing the tumor.

In a block 21 of algorithm 20, a high resolution preoperative MRI image "MRI$_o$" of the patient's head is acquired using an appropriate MRI scanner (not shown) to obtain a three dimensional (3D) image of the patient's brain. The MRI scanner may, by way of example, be an MRI scanner configured to acquire fMRI images and/or DTI MRI images. Image MRI$_o$ is assumed to comprise "M", MRI image slices referred to as slices MRI$_{o,m}$, 1≤m≤M. In a block 22 image MRI$_o$ is processed to identify skull tissue, brain tissue and a region LT$_o$ of the brain comprising lesion tissue to be removed. Any of various brain extraction (BET) algorithms for processing MRI brain images to distinguish brain tissue from skull tissue may be used to segment tissue in image MRI$_o$ and identify lesion tissue region LT$_o$.

In a block 23, a 3D MRI image, "iMRI$_o$", of the patient's head is acquired using a suitable intraoperative, "iMRI", MRI scanner (not shown). Image iMRI$_o$ is assumed to comprise "N*", iMRI image slices, iMRI$_{o,n*}$ 1≤n*≤N*. The MRI scanner that acquires MRI image MRI$_o$, in general has a relatively large FOV, which is generally large enough so that image MRI$_o$ images substantially all of the patient's head and brain. The iMRI scanner on the other hand typically has a comparatively smaller, ellipsoidal shaped FOV, as a result of which image iMRI$_o$ acquired by the iMRI scanner generally images less of the patient's head than image MRI$_o$, and may not image all of the patient's brain.

Figure 1A:
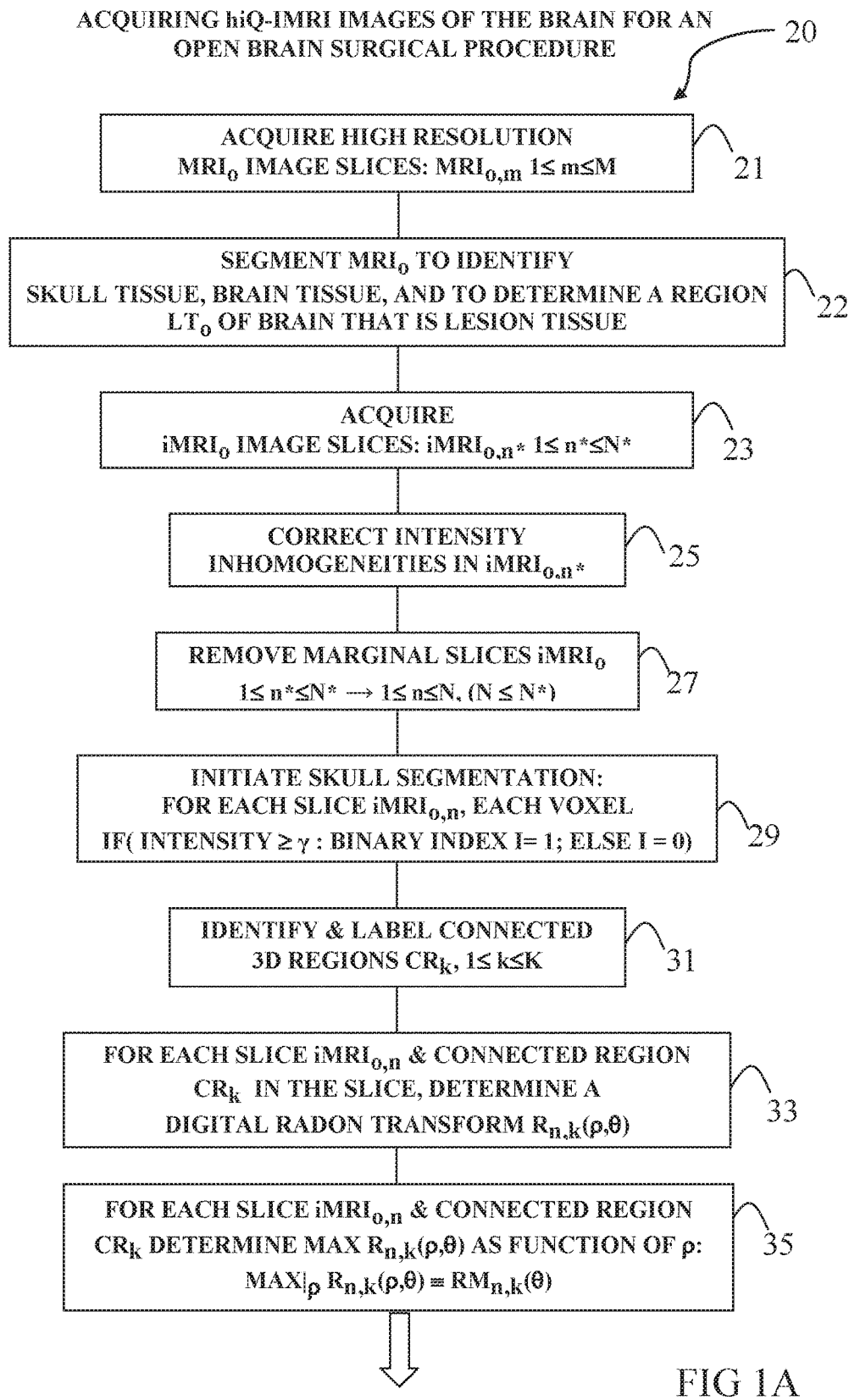
FIGS. 1A-1F show a flow diagram of an algorithm for acquiring a hiQ-iMRI image for an open brain surgery, in accordance with an embodiment of the disclosure.
Figure 1B:
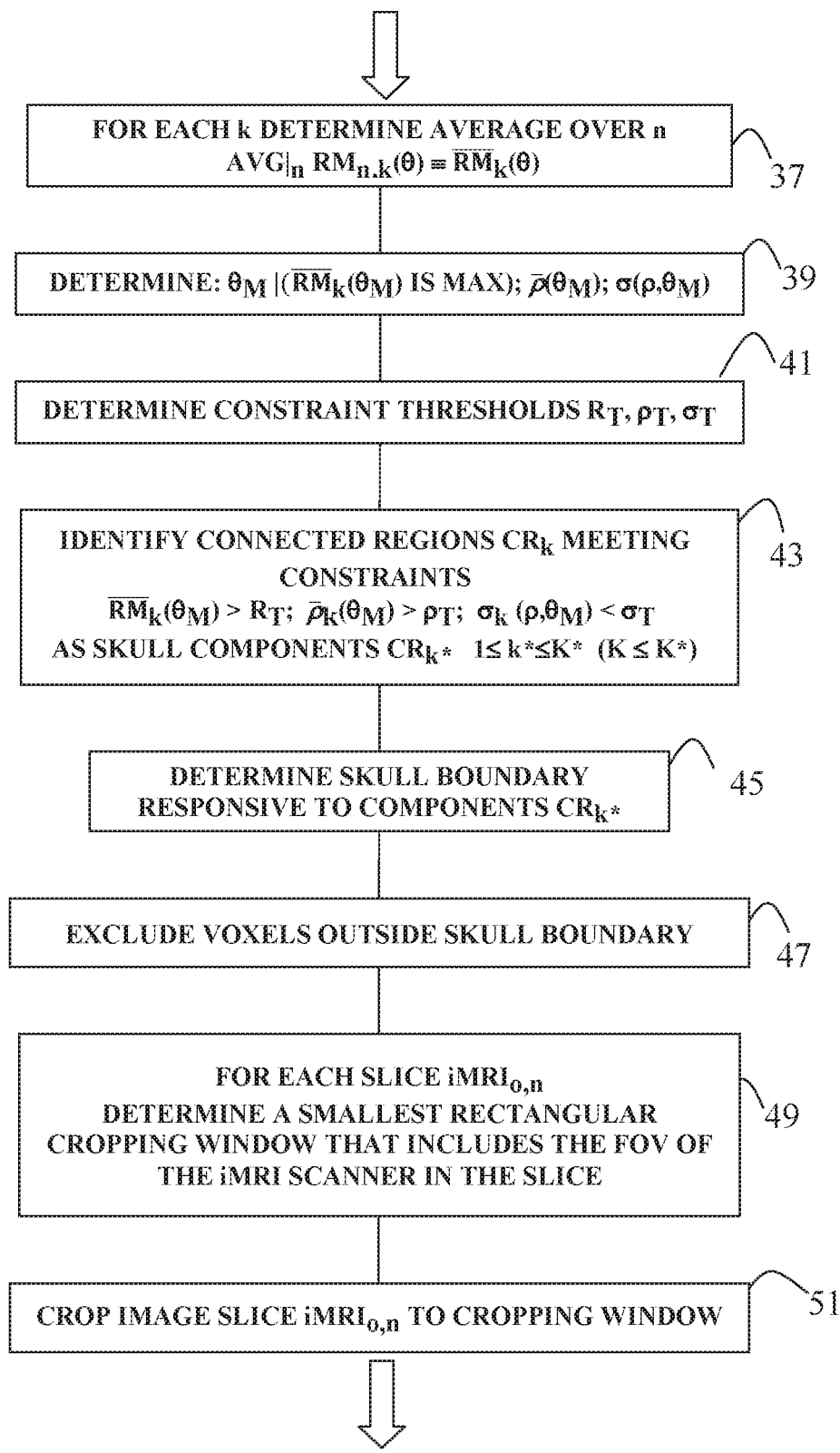
Figure 1C:
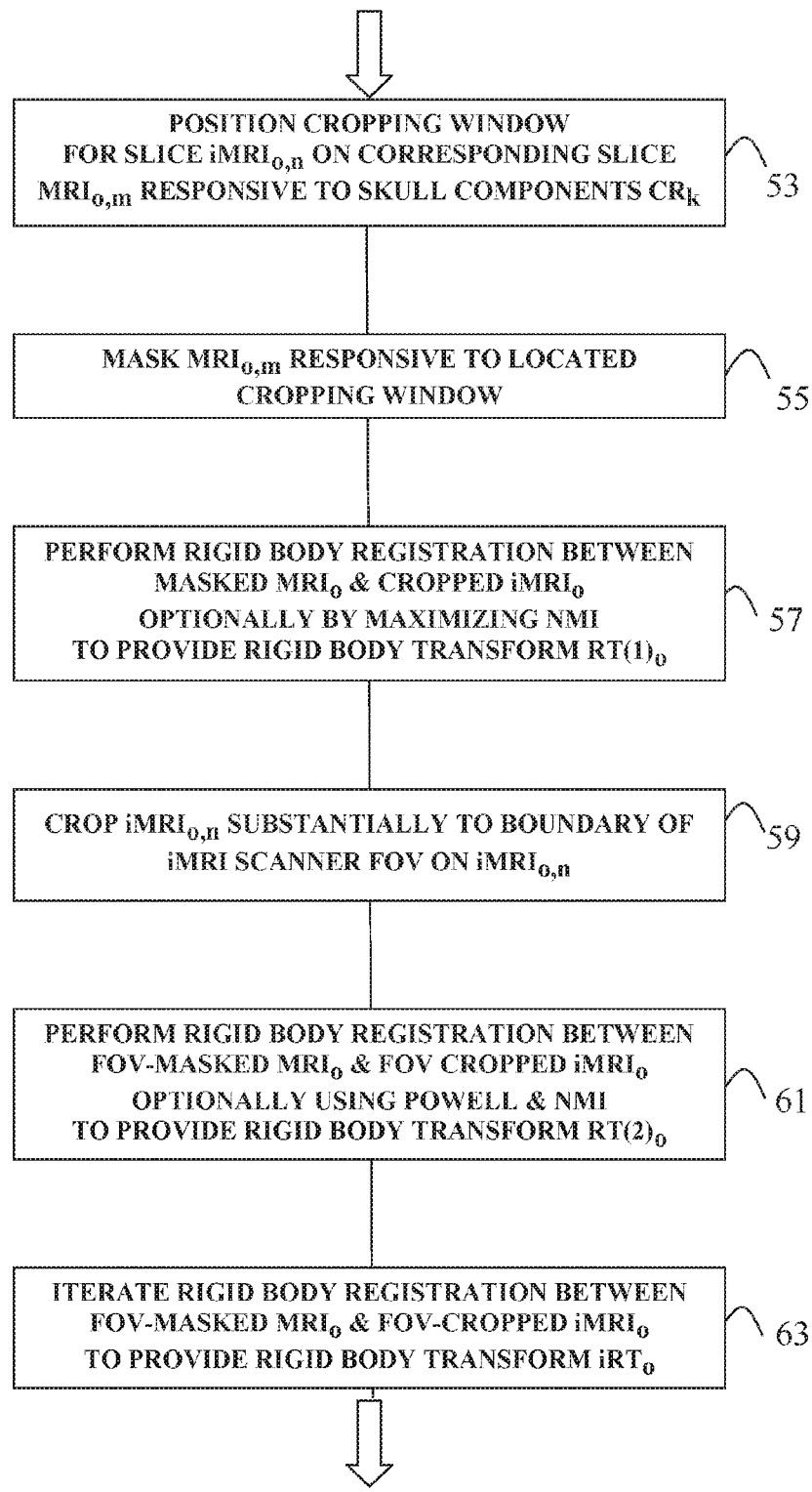
Figure 1D:
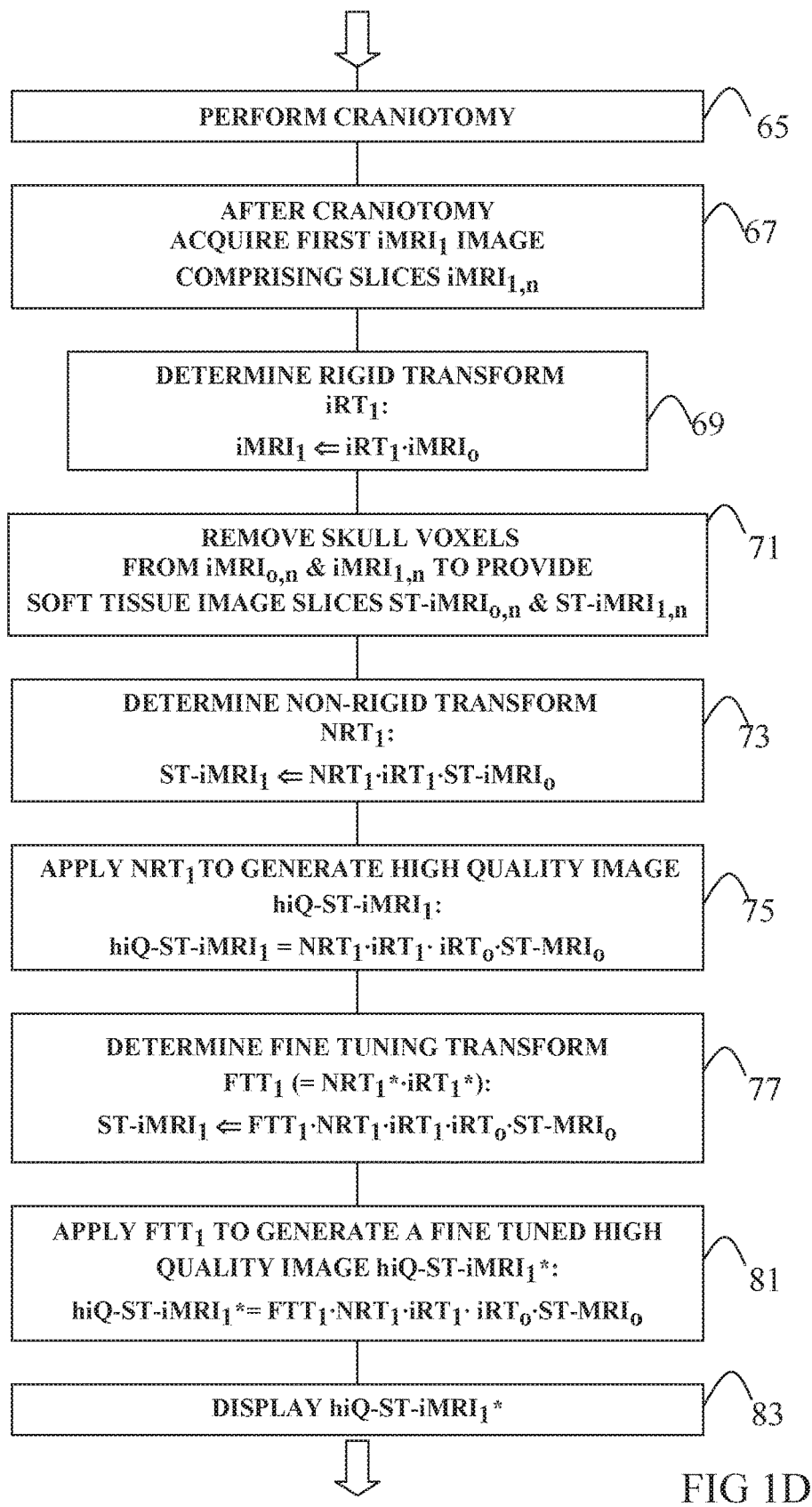
Figure 1E:
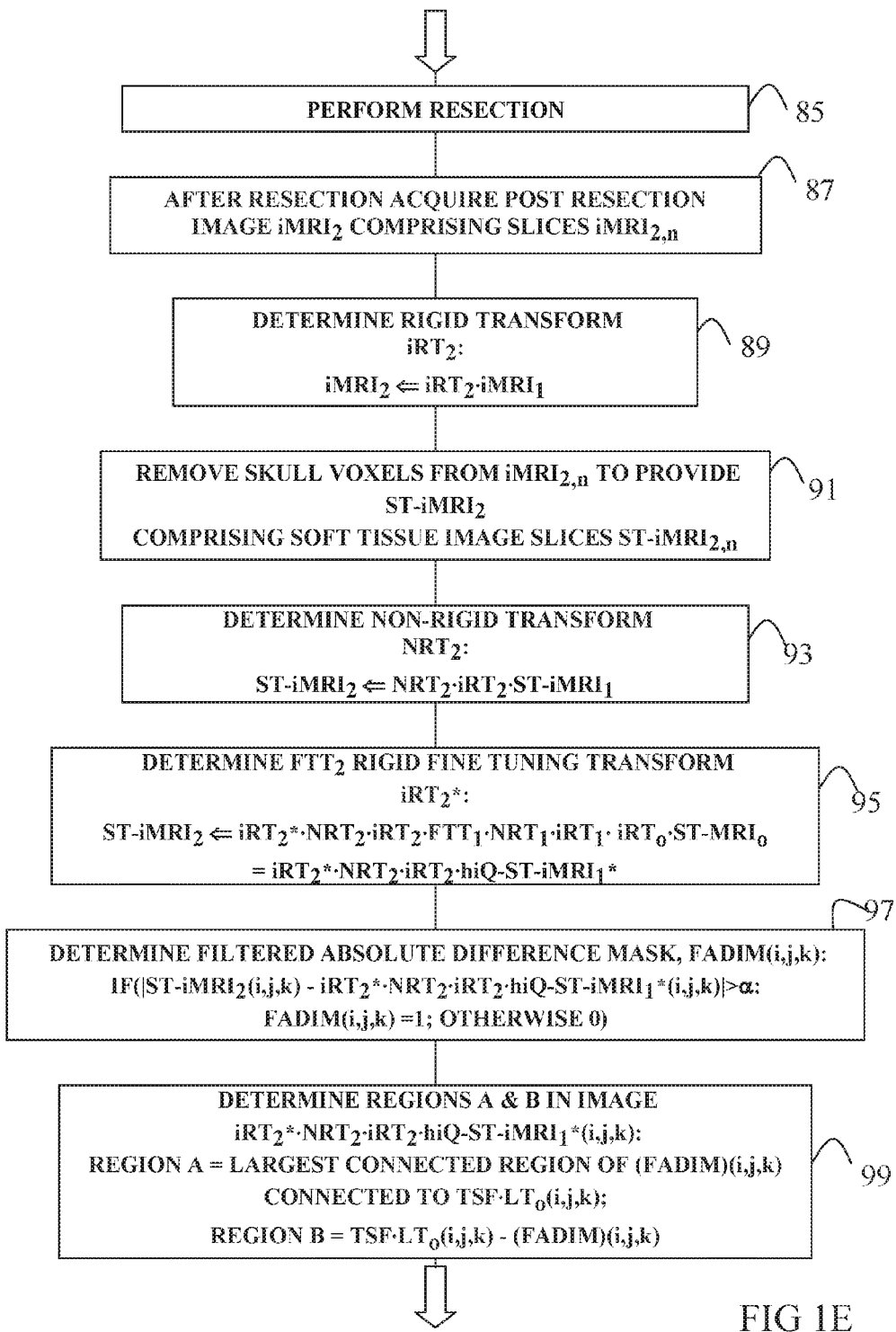
Figure 1F:
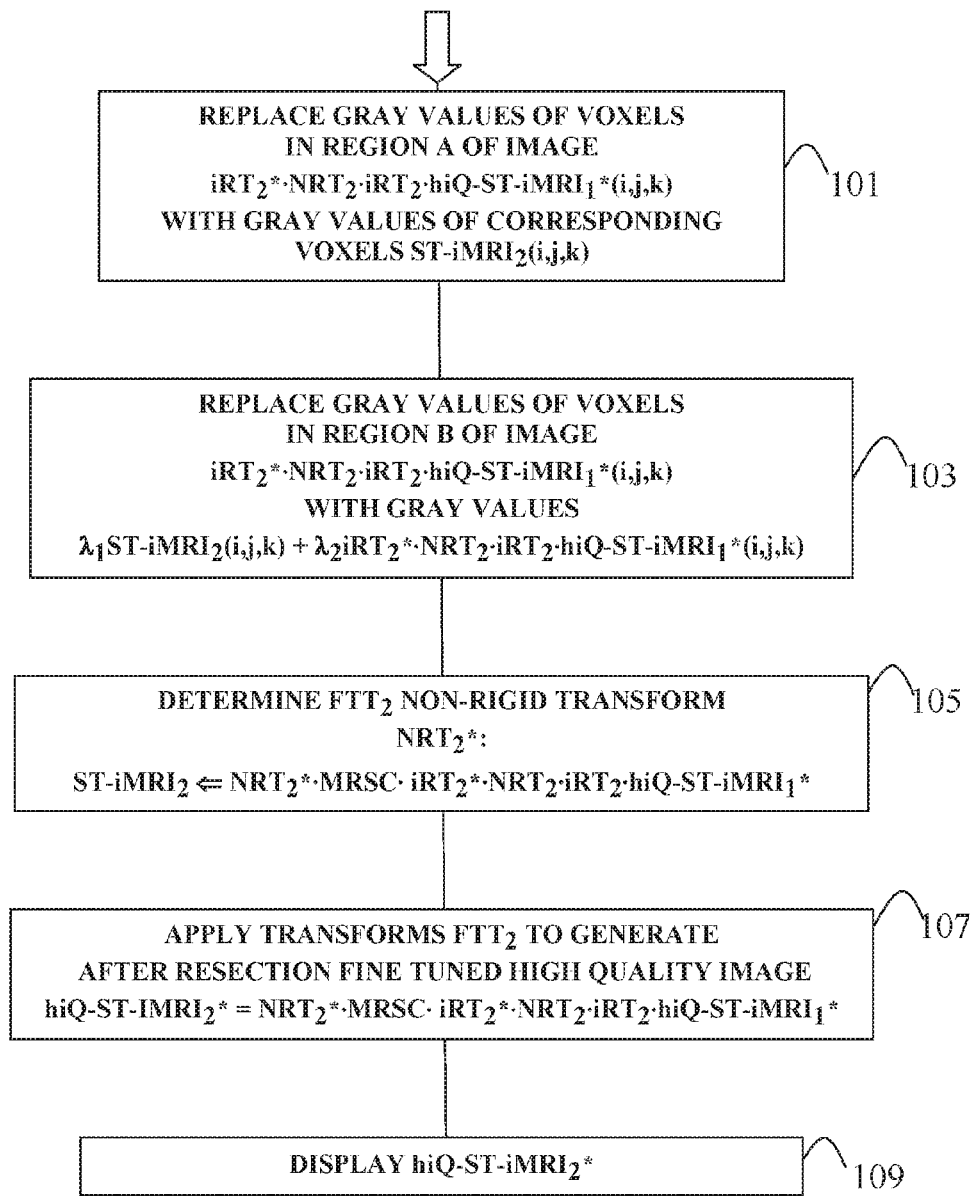
Figure 2:
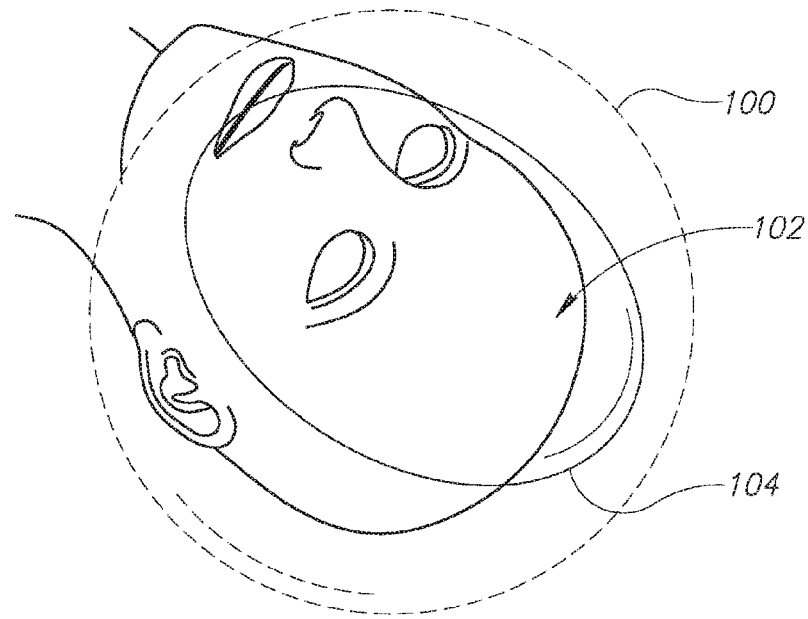
FIG. 2 schematically shows a field of view (FOV) of a conventional MRI scanner and a FOV of an iMRI scanner imaging the head of a same person to acquire an image of the person's brain.

FIG. 2 schematically shows a relatively large FOV indicated by a dashed circle 100, of a conventional MRI scanner imaging the head of a patient 102 about to undergo an open brain medical procedure and a smaller ellipsoidal FOV 104 of an iMRI scanner imaging the head. Whereas the large FOV 100 is able to enclose all of the head of patient 102, enabling the conventional MRI scanner to provide an image of all of the head and brain of patient 102, ellipsoidal FOV 104 encompasses only a portion of the head, as a result of which, the iMRI scanner provides an image of only a portion of the patient's head and brain.

MRI images may exhibit spurious inhomogeneity artifacts in intensities of imaged voxels that may be generated by interaction of the RF flipping fields with tissue in the human body, non-uniform reception of MRI signals by RF receiving antenna, and eddy current generation. The artifacts are generally characterized as a relatively slowly varying bias field as a function of spatial coordinates in the MRI images. The bias field may contribute as much as 30% to MRI signals. Optionally, in a block 25 any of various methods known in the art for estimating and correcting for spurious inhomogeneities in voxel intensities are used to correct for such intensity inhomogeneities in iMRI$_o$ image slices iMRI$_{o,n*}$.

In a block 27, data comprised in "marginal" image slices iMRI$_{o,n*}$ that are located near the extremities of ellipsoidal FOV 104 (FIG. 2) along the ellipsoidal major axis (shown in the discussion of FIG. 3 below), which often comprise data characterized by relatively low SNR, are excluded from further processing by algorithm 20. To determine whether to remove a given image slice iMRI$_{o,n*}$, an intersection area AE$_{o,n*}$ of the image slice with FOV 104 is calculated and an area ratio RA$_{o,n*}$=AE$_{o,n*}$/AE$_{max}$ determined, where AE$_{max}$ is a maximum intersection of the intersections AE$_{o,n*}$ of slices iMRI$_{o,n*}$ with FOV 104. In an embodiment of the disclosure, if RA$_{o,n*}$ for a given n*-th image slice iMRI$_{o,n*}$ is less than a given desired threshold, data in the image slice is excluded from further processing. By way of example, a threshold for RA$_{o,n*}$ may have a value equal to or greater than about 0.5. In an embodiment the threshold may have a value less than or equal to about 0.8. Optionally the threshold is equal to about 0.7. For convenience of presentation, a remaining "N" image slices iMRI$_{o,n*}$ that are not excluded from further processing as a result of their ratio RA$_{o,n*}$ being too low, are indexed by an index "n" and are denoted iMRI$_{o,n}$, 1≤n≤N.

Figure 3:
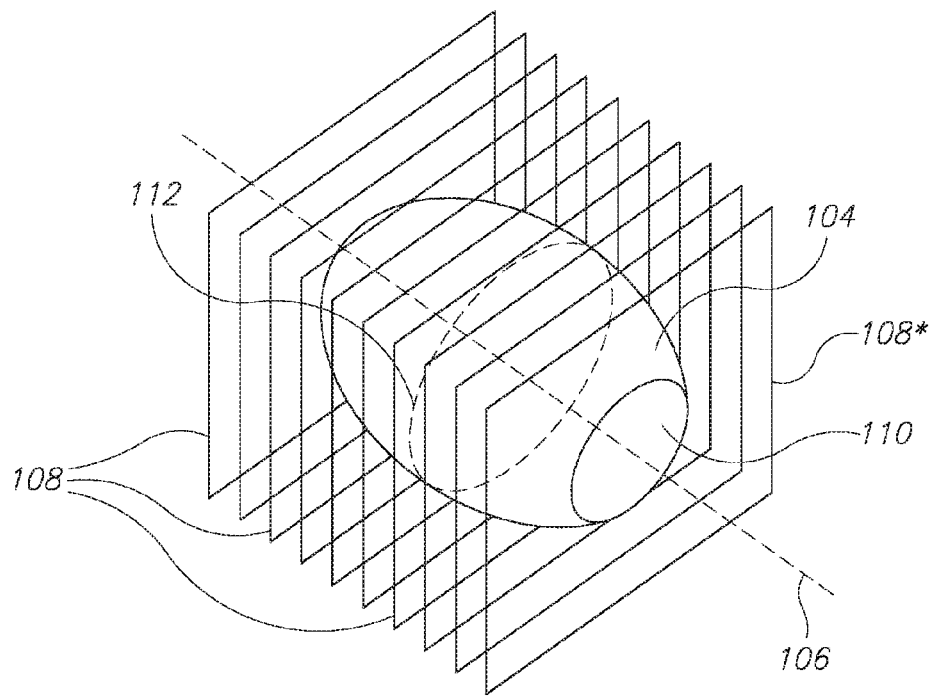
FIG. 3 schematically illustrates a method of removing extraneous information from an iMRI image, in accordance with an embodiment of the disclosure.

FIG. 3 schematically shows FOV 104, its major axis 106, and exemplary slices iMRI$_{o,n*}$ 108 in image iMRI$_o$ that intersect FOV 104. An image slice 108 distinguished by a reference numeral 108* is schematically shown having an intersection 110 with FOV 104. A dashed ellipse 112 indicates a periphery of a maximum intersection AE$_{max}$ for determining area ratios RA$_{o,n*}$, in accordance with an embodiment of the disclosure.

Figure 4A:
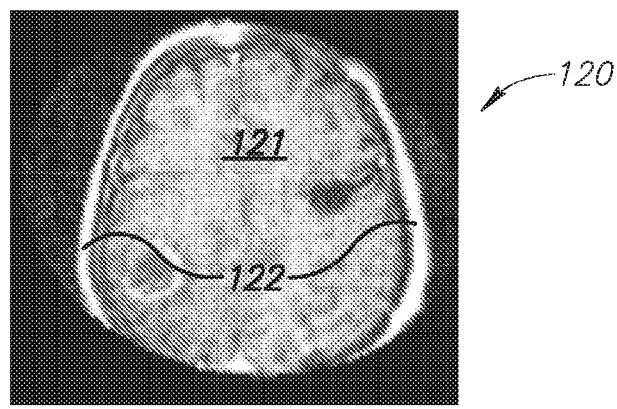
FIGS. 4A-4D schematically illustrates segmenting skull tissue imaged in an image slice of a preoperative iMRI$_o$ image, in accordance with an embodiment of the disclosure.
Figure 4B:
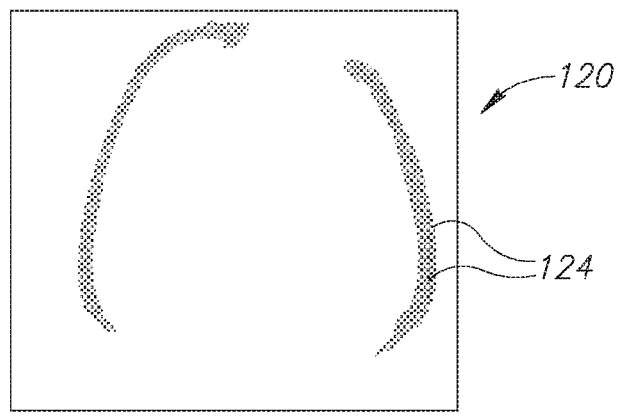

In a block 29, tissue segmentation to identify skull tissue is initiated and voxels in each image slice iMRI$_{o,n}$ having intensity greater than a given threshold γ are optionally labeled with a binary "1" to indicate that they are candidates for imaging skull tissue. Voxels exhibiting intensity less than γ in the image slice are optionally labeled with a binary "0" to indicate that they are not considered candidates for imaging bone tissue. FIG. 4A schematically shows a given example image slice iMRI$_{o,n}$ labeled 120 that images a portion of the head of patient 102 and comprises brain and skull tissue 121 and 122 respectively. FIG. 4B schematically shows a map of candidate skull tissue voxels 124 assigned a binary 1 following labeling responsive to voxel image intensities and threshold γ. In FIG. 4B, voxels that are not considered to be candidates for imaging skull tissue 122 (FIG. 4A), such as voxels imaging brain tissue 121, (FIG. 4A), are not shown.

Figure 4C:
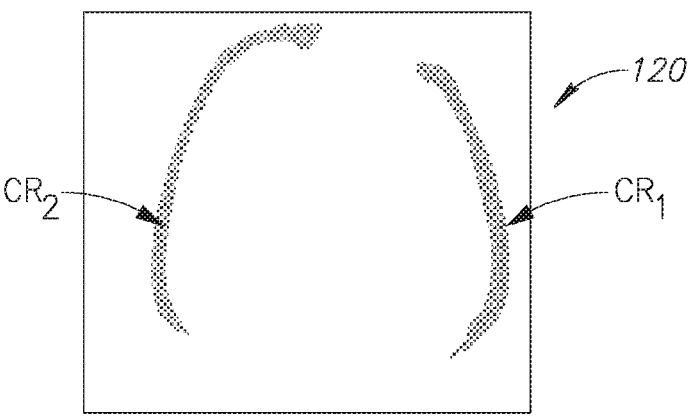

Optionally, in a block 31 voxels labeled as skull candidate voxels in image slices iMRI$_{o,n}$ undergo 3D connected component labeling to identify connected regions in image iMRI$_o$ that are candidates for components of the patient's skull. Connected 3D labeling is assumed to identify "K" 3D distinct and separate, connected regions CR$_k$, 1≤k≤K that are candidates for skull components. Optionally, connected component labeling comprises 26 neighbor connectivity labeling. FIG. 4C schematically shows two distinct and separate, connected regions arbitrarily labeled CR$_1$ and CR$_2$ in example image slice 120.

In order to determine whether a given 3D connected region, CR$_k$, identified in image iMRI$_o$ is to be considered a component of the skull of patient 102, optionally in a block 33, a "digital" Radon transform of the connected region is calculated for the given connected region in each image slice iMRI$_{o,n}$ in which the connected region appears. The digital Radon transform R$_{n,k}(\rho,\theta)$ for the k-th connected region in the n-th image slice iMRI$_{o,n}$ is a function of an angle $\theta$ and a distance $\rho$.

The angle $\theta$, also referred to as a "Radon angle", is an angle that a line, also referred to as a "Radon line", extending from an origin of a coordinate system in image slice iMRI$_{o,n}$ makes with an axis of the coordinate system. The origin may be located at a centroid of image slice iMRI$_{o,n}$ or at an intersection of the image slice with an axis of the elliptical FOV of the iMRI scanner that acquired the image slice. Distance $\rho$, also referred to as a "Radon distance", is a distance measured from the origin along the Radon line. The digital Radon transform for a given angle $\theta$ and a distance $\rho$ has a value equal to a number of voxels intersected by a line, referred to as a projection line, that is perpendicular to and passes through the Radon line at angle $\theta$ at a distance $\rho$ from the origin.

Figure 4D:
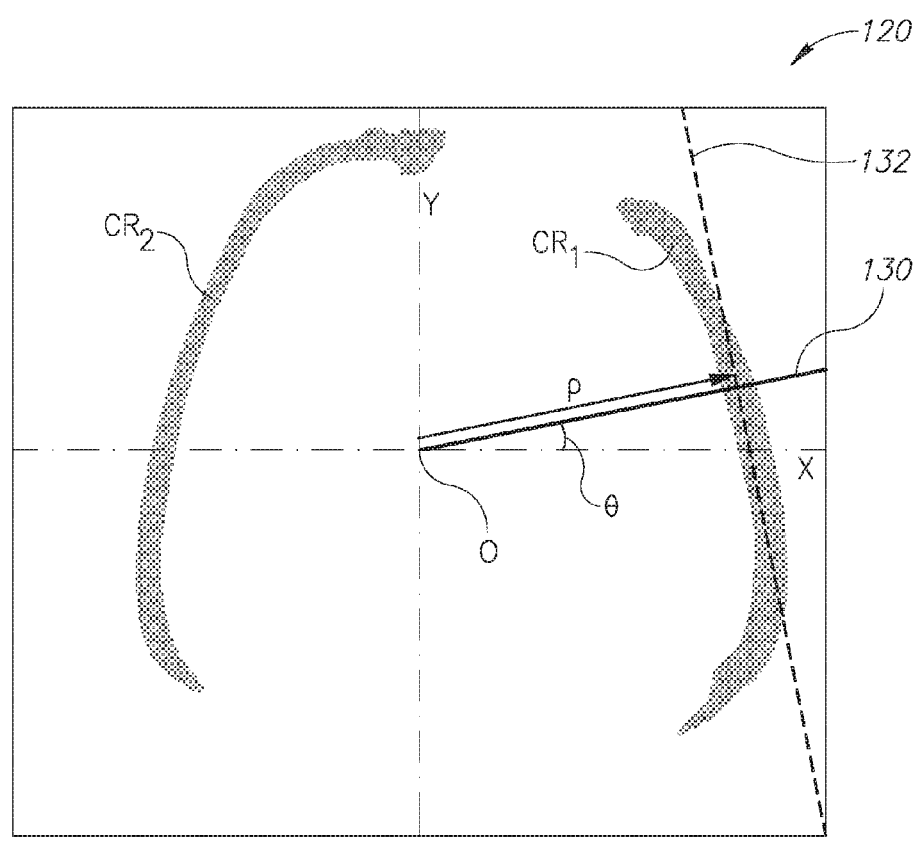

FIG. 4D schematically shows example image slice 120 and connected regions CR$_1$ and CR$_2$ as shown in FIG. 4C, with an addition of an xy-coordinate system having origin O and a Radon line 130 that make an angle $\theta$, with the x-axis. The digital Radon transform R$_{n,k}(\rho,\theta)$ for CR$_1$ in example image slice 120, at angle $\theta$ and a distance $\rho$ along Radon line 130 is a count of a number of voxels in CR$_1$ through which a projection line 132 passes. Projection line 132 is perpendicular to Radon line 130 at a distance $\rho$ from origin O.

Optionally, in a block 35, for each CR$_k$ in each slice iMRI$_{o,n}$ the maximum value RM$_{n,k}(\theta)$ of R$_{n,k}(\rho,\theta)$ as a function of $\rho$ for each angle $\theta$ is determined. And in a block 37 an average $\overline{RM}_k(\theta)$ of RM$_{n,k}(\theta)$ for each Radon angle $\theta$ over image slices iMRI$_{o,n}$ in which CR$_k$ appears is determined.

In a block 39, for each CR$_k$, a Radon angle $\theta_M$ for which $\overline{RM}_k(\theta_M)$ is a maximum, and an average $\overline{\rho}(\theta_M)_k$ Radon distance at angle $\theta_M$ for the image slices iMRI$_{o,n}$ in which CR$_k$ appears are determined. A standard deviation $\sigma(\theta_M)_k$ for $\rho(\theta_M)_k$ is also determined. In a block 41, constraint thresholds R$_T$, $\rho_T$, $\sigma_T$ for $\overline{RM}_k(\theta_M)$, $\overline{\rho}(\theta_M)_k$, and $\sigma(\theta_M)_k$ respectively may be determined. In a block 43, connected regions CR$_k$ that meet constraints $\overline{RM}_k(\theta_M)>R_T$, $\overline{\rho}(\theta_M)_k>\rho_T$, and $\sigma(\theta_M)_k<\sigma(\theta_M)_k$ are identified as components of the skull of patient 102. For convenience of presentation the connected components satisfying the constraints are indexed by an index k* and are referred to as skull components CR$_k$*, ≤1≤k*≤K* (K≤K*).

In an embodiment of the disclosure values for the constraint thresholds are determined using an empirical trial and error procedure. In the empirical procedure, different constraint threshold values may be used to process image slices iMRI$_{o,n}$ and advantageous constraint values for R$_T$, $\rho_T$, $\sigma_T$ chosen responsive to visual evaluation of how well the constraints function for identifying skull components CR$_{k*}$. In an embodiment of the disclosure, R$_T$ is greater than or equal to about 20 voxels. Optionally, R$_T$ is greater than or equal to about 25 voxels. In an embodiment of the disclosure $\rho_T$ is greater than or equal to about 12 voxels. Optionally, $\rho_T$ is greater than or equal to about 15 voxels. Optionally, $\sigma_T$ is less than or equal to about 0.15 $\overline{RM}_k(\theta_M)$. In an embodiment of the disclosure, $\sigma_T$ is less than or equal to about 0.1 $\overline{RM}_k(\theta_M)$.

Optionally, in a block 45, for each image slice iMRI$_{o,n}$, a skull boundary is determined for the slice responsive to skull components CR$_{k*}$ appearing in the slice, and in a block 47 voxels outside of the skull boundary are, optionally, excluded from further processing in algorithm 20. In an embodiment of the disclosure, the skull boundary in a slice lies along an outer boundary of the skull components imaged in the slice as measured from origin O of the coordinate system used in determining the Radon transform for the slice. In an embodiment of the disclosure, the outer boundary is substantially coincident with a boundary line for which the digital Radon transform along any given Radon line is zero for any distance greater than an intersection of the boundary line with the given Radon line.

In a block 49 a substantially smallest polygonal cropping window may be determined for each image slice iMRI$_{o,n}$ that includes substantially all of the area of an intersection of the head of patient 102 with the FOV of the iMRI scanner that acquired the image slice. Optionally, the polygonal cropping window is square or rectangular, hereinafter generically referred to as a rectangular. In a block 51, each image slice iMRI$_{o,n}$ is cropped to its cropping window. The region of an image slice iMRI$_{o,n}$ to which the image slice is cropped may be referred to as a cropped image slice iMRI$_{o,n}$.

Figure 5A:
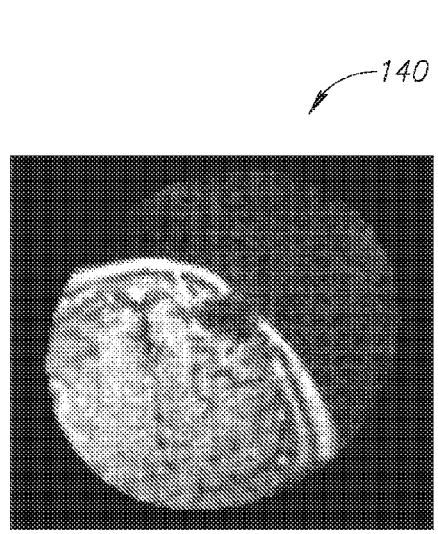
FIGS. 5A-5E schematically illustrates cropping an image slice of a preoperative iMRI$_o$ image responsive to an iMRI image, in accordance with an embodiment of the disclosure.
Figure 5B:
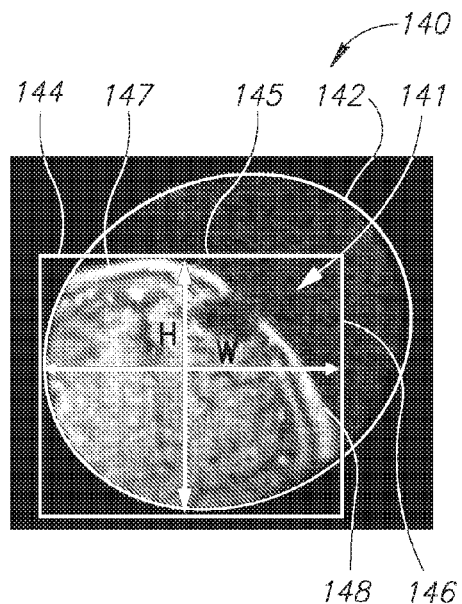

FIG. 5A schematically shows an iMRI$_{o,n}$ example image slice 140 in which only a portion of the skull and brain of patient 102 is imaged because ellipsoidal FOV 104 (FIG. 3) of the iMRI scanner imaging image slice 140 was too small to include all of the skull and brain. FIG. 5B schematically shows a perimeter 142 of an intersection of ellipsoidal FOV 104 with image slice 140 and a rectangular cropping window 144 for cropping image slice 140. Cropping window 144 has a top edge 145 and an adjacent side edge 146. "Top" and "side" skull features 147 and 148 are located adjacent and optionally substantially tangent to top and edge sides 145 and 146 respectively. A region 141 of image slice 140 bounded by cropping window 144 may be referred to as cropped image slice 141.

In a block 53, the cropping window determined for each image slice iMRI$_{o,n}$, by way of example cropping window 144 schematically shown in FIG. 5B for example image slice 140, is positioned on a corresponding image slice MRI$_{o,m}$ of image MRI$_o$. In accordance with an embodiment of the disclosure, positioning the cropping window determined for an image slice iMRI$_{o,n}$ on a corresponding image slice MRI$_{o,m}$ comprises positioning the cropping window so that features of the skull in image slice MRI$_{o,m}$ that are common to skull features in image slice iMRI$_{o,n}$ are within the cropping window positioned on image slice MRI$_{o,m}$.

It is noted that in general a number M of slices MRI$_{o,m}$ in image in MRI$_o$ is not equal, to and is in general larger than the number N of slices iMRI$_{o,n}$ in image iMRI$_o$. To establish corresponding slices in images MRI$_o$ and iMRI$_o$ voxels in slices MRI$_{o,m}$ and/or iMRI$_{o,n}$ may be suitably binned and/or spatially resampled and interpolated, so that there are same number of slices in iMRI$_{o,n}$ and MRI$_{o,m}$. It is assumed hereinafter that voxels in MRI$_{o,m}$ and/or iMRI$_{o,n}$ have been binned so that M=N. It is further assumed that where advantageous or required, images iMRI$_o$ and MRI$_o$ may have been processed so that 3D pitch of voxels in MRI$_o$ is substantially the same in iMRI$_o$.

In an embodiment of the disclosure, positioning the cropping window in image slice MRI$_{o,m}$ comprises positioning the cropping window so that skull features in image slice iMRI$_{o,n}$ that are located along a top edge and an adjacent side edge of the cropping window are substantially homologous with the same top and edge sides of the cropping window when the cropping window is positioned in corresponding image slice MRI$_{o,m}$. Optionally, positioning the cropping window in corresponding image slice MRI$_{o,m}$ comprises determining a transform that translates the cropping window from a coordinate system that locates features in image slice $iMRI_{o,n}$ to a coordinate system that is used to locate features in the corresponding image slice $MRI_{o,m}$.

Figure 5C:
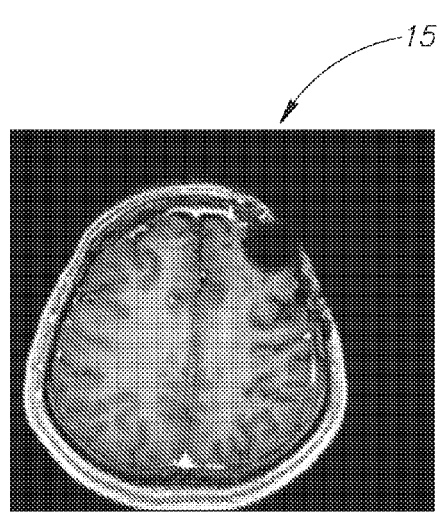
Figure 5D:
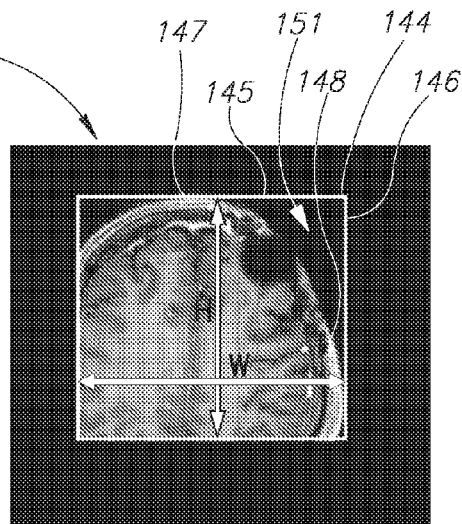

FIG. 5C schematically shows an example $MRI_{o,m}$ image slice 150 corresponding to $iMRI_{o,n}$ example $iMRI_{o,n}$ image slice 140 shown in FIGS. 5A and 5B. FIG. 5D schematically shows cropping window 144 shown in FIG. 5B positioned on example $MRI_{o,m}$ image slice 150 so that skull features 147 and 148 located along top and side edges 145 and 146 respectively in example $iMRI_{o,n}$ image slice 140 (FIGS. 5A and 5B) are similarly located relative to top and side edges 145 and 146 of the cropping window in example $MRI_{o,m}$ image slice 150.

In a block 55, a region of each image slice $MRI_{o,m}$ located within the cropping window, for example a region 151 in FIG. 5D of example $MRI_{o,m}$ image slice 150 within cropping window 144, is masked, and may be referred to as a masked image slice $MRI_{o,m}$. In a block 57, the 3D masked image, $MRI_{o}$, of the brain defined by masked image slices $MRI_{o,m}$, $1 \leq m \leq M$ is registered to the corresponding 3D cropped image, $iMRI_{o}$, of the brain defined by cropped image slices $iMRI_{o,n}$, $1 \leq n \leq N$. The registration provides a first, "coarse" rigid body registration transform $RT(1)_o$ of the masked brain image $MRI_o$ to the cropped brain image $iMRI_o$.

For example, in accordance with an embodiment of the disclosure, the 3D masked image $MRI_o$ defined by masked image slices $MRI_{o,m}$, such as example $MRI_{o,m}$ image slice 150 shown in FIG. 5D and comprising region 151 masked responsive to cropping window 144, may be registered to 3D cropped image $iMRI_o$ defined by cropped image slices $iMRI_{o,n}$, such as cropped example $iMRI_{o,n}$ image slice 140 shown in FIG. 5B and comprising a region 141 within cropping window 144.

Optionally, the rigid body registration of masked image $MRI_o$ to cropped image $iMRI_o$ is performed by maximizing their normalized mutual information (NMI). Maximizing NMI to determine rigid body registration transform $RT(1)_o$ may be performed using a Powell algorithm to find rigid body transform parameters that maximize the NMI.

Figure 5E:
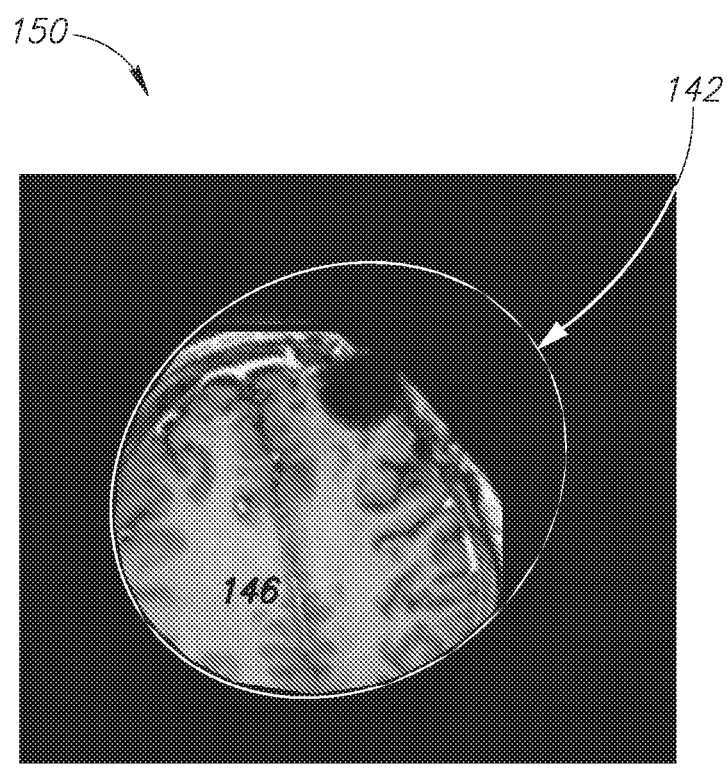

Following coarse registration of image $MRI_o$ to image $iMRI_o$, optionally using rectangular cropping windows, in a block 59, each image slice $iMRI_{o,n}$ is cropped substantially to a boundary of the ellipsoidal FOV of the scanner that acquired image $iMRI_o$ to provide an "FOV cropped" image slice $iMRI_{o,n}$. The ellipsoidal FOV is also used to mask the transformed slices $RT(1)_o \cdot MRI_{o,m}$ that define the transformed 3D image $RT(1)_o \cdot MRI_o$ of the brain. FIG. 5E schematically shows the example $MRI_{o,m}$ image slice 150 masked responsive to the ellipsoidal FOV, having perimeter 142 in slice 150, after the slice has been transformed by transform $RT(1)_o$. Operation of the transform $RT(1)_o$ has rotated the image of brain tissue in $MRI_{o,m}$ example slice 150 counterclockwise so that the image in the example slice 150 approaches congruence with image of brain tissue in $iMRI_{o,n}$ example slice 140 shown in FIG. 5B from image $iMRI_o$. After masking, substantially only voxels comprised in example image slice 150 that are located within ellipsoidal contour 142 are processed in accordance with algorithm 20.

Optionally, in a block 61, the FOV masked, transformed image $RT(1)_o \cdot MRI_o$ comprising example slice 150 shown in FIG. 5E is registered to 3D image $iMRI_o$ to provide a second rigid body registration transform $RT(2)_o$. Transform $RT(2)_o$ transforms FOV masked 3D image $RT(1)_o \cdot MRI_o$ to FOV cropped 3D image $iMRI_o$. Optionally, $RT(2)_o$ is determined responsive to maximizing NMI between FOV masked transformed image $RT(1) \cdot MRI_o$ and the FOV cropped image $iMRI_o$. In a block 63, transformed image $RT(2)_o \cdot RT(1)_o \cdot MRI_o$ is masked by the ellipsoidal FOV of the iMRI, scanner and registered to FOV cropped image $iMRI_o$. The procedure is iterated until a criterion for ending iteration following a j-th iteration is satisfied and an acceptable transform $iRT_o = RT(j)_o \ldots RT(2)_o \cdot RT(1)_o$ from $MRI_o$ to $iMRI_o$ is acquired. Optionally, the criterion is satisfied when a predetermined number of iterations is performed. In an embodiment of the disclosure, the criterion is satisfied at the j-th iteration when a cost function that measures how well the image $MRI_o$ transformed by transform $RT(j)_o \ldots \cdot RT(2)_o \cdot RT(1)_o$ matches image $iMRI_o$ reaches a desired value.

Following determination of rigid body registration transform $iRT_o$ in block 63, craniotomy is performed optionally in a block 65 to remove of a portion of the skull of patient 102 and expose the patient's brain to enable performance of the medical procedure for which the MRI images of the patients head are acquired. In a block 67, a first post craniotomy MRI image, $iMRI_1$, defined by image slices $iMRI_{1,n}$ is acquired, optionally using the same iMRI scanner used to acquire $iMRI_o$.

In an embodiment of the disclosure, the $MRI_o$ image is registered to the $iMRI_1$ image using a rigid transform and a non-rigid transform to provide a relatively high resolution, high quality interoperative image $hiQ$-$iMRI_1$ for a time $t_1$ at which $iMRI_1$ is acquired. Optionally, the rigid transform comprises a transform "$iRT_1$", determined in a block 69, that transforms image $iMRI_o$ to $iMRI_1$. Since images $iMRI_o$ and $iMRI_1$ are, optionally, both acquired by the same iMRI scanner transform $iRT_1$ may be determined, for example by maximizing NMI between $iRT_1 \cdot iMRI_o$ and $iMRI_1$, optionally using a Powell algorithm, in a single step procedure rather than an iterated procedure as optionally used to determine $iRT_o$.

Determining a transform that "transforms", "registers" or "warps" a first image to a second image by operating to optimize performance of the transform may be indicated by a symbol "⇐" in an expression relating the first and second images to the transform. For example, in the expression $iMRI_1 \Leftarrow iRT_1 \cdot iMRI_o$ in block 69, ⇐ indicates that $iRT_1$ is determined in accordance with a suitable procedure that operates to optimize operation of $iRT_1$ and reduce difference between image $iMRI_1$ and image $iRT_1 \cdot iMRI_o$.

In an embodiment of the disclosure, the non-rigid transform comprises a transform $NRT_1$, which operates, as discussed below, to transform $iRT_1 \cdot iMRI_o$ to $iMRI_1$ and provide a high resolution image of brain tissue substantially for time $t_1$ at which $iMRI_1$ is acquired. Whereas presence of skull tissue in $iMRI_o$ and $iMRI_1$ may be advantageous in determining rigid transform such as $iRT_1$, the presence of bone tissue in image $iMRI_o$ and image $iMRI_1$ may not be advantageous for determining the non-rigid transform $NRT_1$ which is intended to register brain tissue in image $iMRI_o$ to brain tissue in image $iMRI_1$, which may, and generally is deformed as a result of craniotomy. Images of skull tissue in image slices $iMRI_{o,n}$ of image $iMRI_o$ and corresponding image slices $iMRI_{1,n}$ of image $iMRI_1$ may compromise determination of $NRT_1$, and as a result degrade accuracy with which $NRT_1$ is able to provide non-rigid registration of brain tissue in $iMRI_o$ to brain tissue in $iMRI_1$. In the presence of images of bone tissue, an algorithm that operates to determine non-rigid transform $NRT_1$ may, in order to provide an overall satisfactory measure of accuracy of registration, sacrifice accuracy of registration of brain tissue to provide accuracy of registration of bone tissue.

However, during brain surgery, fidelity and resolution of an image of brain tissue in a target site of a procedure is generally of particular advantage. Therefore, in an embodiment of the disclosure, in a block 71, prior to determining a non-rigid transform, such as $NRT_1$, that registers image $iMRI_o$ and image $iMRI_1$ to each other and accounts for deformation of brain tissue in $iMRI_1$ relative to brain tissue in $iMRI_o$, voxels in the images that image skull tissue are removed. In an embodiment, to remove skull tissue voxels, skull tissue identified in image $MRI_o$ as noted in block 22 is used to define a binary mask that distinguishes skull tissue from soft tissue. The binary mask transformed by rigid transform $iRT_o$ and projected to image $iMRI_o$ may be used to mask away bone tissue voxels in image $iMRI_o$. The binary mask transformed by rigid transform $iRT_1 \cdot iRT_o$ and projected to image $iMRI_1$ may be used to mask away bone tissue voxels in image $iMRI_1$. In an embodiment, skull tissue identified in image $iMRI_o$, as for example described above with reference to blocks 29-43, may be used to define a binary skull tissue mask. The skull tissue mask may be used to remove skull tissue from image $iMRI_o$, and transformed by rigid transform $iRT_1$ may be used to mask away skull tissue in image $iMRI_1$. A skull tissue mask for removing skull tissue in image $iMRI_1$ may be determined responsive to skull tissue identified in both $MRI_o$ and $iMRI_o$ and suitably transformed by a rigid body transform to remove skull tissue from images $iMRI_o$ and $iMRI_1$.

It is noted that whereas in the above discussion skull tissue is described as being removed after rigid body transform $iRT_1$ is determined. However, in an embodiment of the specification skull tissue may be removed prior to determining $iRT_1$ to mitigate possible deleterious effects on accuracy of a determined $iRT_1$ for transforming brain tissue. Such effects may result from changes in the shape and/or size of a volume of cerebral spinal fluid (CSF) that fills the skull as a result of a shift of the brain relative to the skull, which may result from craniotomy.

For convenience of presentation, images and image slices from which skull voxels are removed are prefixed with "ST" to indicate they contain only voxels that image soft tissue—that is, brain tissue. Images $iMRI_o$ and $iMRI_1$ after removal of voxels that image skull tissue may be referred to as $ST\text{-}iMRI_o$ and $ST\text{-}iMRI_1$ images, and slices in the images may be referred to as slices $ST\text{-}iMRI_{o,n}$ and $ST\text{-}iMRI_{1,n}$ respectively.

In a block 73, algorithm 20 determines non-rigid transform $NRT_1$ which transforms $ST\text{-}iMRI_o$ to $ST\text{-}iMRI_1$, after $ST\text{-}iMRI_o$ is transformed by rigid transform $RT_1$ in accordance with an equation $ST\text{-}iMRI_1 \Leftarrow NRT_1 \cdot iRT_1 \cdot ST\text{-}iMRI_o$.

Let the spatial vectors that define locations of brain tissue voxels imaged in image $iRT_1 \cdot ST\text{-}iMRI_o$ (that is, image $ST\text{-}iMRI_o$ after transformation under $iRT_1$) be represented by k and have, optionally, Cartesian spatial coordinates $x_1$, $x_2$, and $x_3$. Let spatial vectors defining locations of brain tissue voxels imaged in image $ST\text{-}iMRI_1$ be represented by $\bar{x}'$ and have spatial coordinates $x'_1$, $x'_2$, and $x'_3$. Image $iRT_1 \cdot ST\text{-}iMRI_o$ may therefore be written to explicitly show dependence on location $\bar{x}$ as $iRT_1 \cdot ST\text{-}iMRI_o(\bar{x})$. And image $ST\text{-}iMRI_1$ may be written $ST\text{-}iMRI_1 (\bar{x}')$ to explicitly show dependence on location $\bar{x}'$. Transform $NRT_1$ operates to transform $\bar{x} \rightarrow \bar{x}'$, and may be written as a function of $\bar{x}$ that returns a value for $\bar{x}'$ for a given value for $\bar{x}$. In symbols, the operation of $NRT_1(\bar{x})$ is given by an expression $\bar{x}' = NRT_1(\bar{x})$.

In an embodiment of the disclosure, non-rigid transform $NRT_1(\bar{x})$ is defined as a transform that warps points at locations $\bar{x}(k)$ ($1 \leq k \leq K$), also referred to as control points $\bar{x}_k$, comprised in a regular lattice of points in image $iRT_1 \cdot ST\text{-}iMRI_o(\bar{x})$, to points in image $ST\text{-}iMRI_1$ by translating lattice points $\bar{x}(k)$ by vector displacements $\overline{D}(k)$ respectively. In an embodiment $NRT_1(\bar{x})$ is a B-spline transform that warps points intermediate of control points $\bar{x}_k$ responsive to B-spline polynomials. Optionally, the B-spline polynomials are cubic B-splines, $\beta^3(\cdot)$.

In an embodiment of the disclosure $NRT_1(\bar{x}) = \bar{x}' = \bar{x} + \overline{D}(k)$, where $\overline{D}(k) = \Sigma_k [\beta^3(|(\bar{x}-\bar{x}_k)/\bar{\sigma}|)] \overline{P}(k)$, and $\bar{\sigma}$ is a control point lattice spacing vector having components $\sigma_1$, $\sigma_2$, and $\sigma_3$ that define spacing between control points in directions indicated by subscripts 1, 2, and 3 respectively. For a given point at location $\bar{x}$ in image $iRT_1 \cdot ST\text{-}iMRI_o(\bar{x})$, the argument of $\beta^3$, $|(\bar{x}-\bar{x}(k))/\bar{\sigma}|$, is equal to $[(x_1-x(k)_1)^2/\sigma_1^2 + (x_2-x(k)_2)^2/\sigma_2^2 + (x_3-x(k)_3)^2/\sigma_3^2]^{1/2}$. For convenience of presentation let $X = |(\bar{x}-\bar{x}(k))/\bar{\sigma}|$. In an embodiment of the disclosure: $\beta^3(X) = \frac{2}{3} - X^2 + X^3$ if $0 \leq X < 1$; $\beta^3(X) = (2-X)^3/6$ if $1 \leq X < 2$; and $\beta^3(X) = 0$ if $2 \leq X$.

For a given $\bar{\sigma}$, and thereby a given lattice configuration of control points, displacement vectors $\overline{D}(k)$ are determined so that transform $NRT_1(\bar{x})$ provides an advantageous registration of image $iRT_1 \cdot ST\text{-}iMRI_o(\bar{x})$ to image $ST\text{-}iMRI_1$, which is characterized by a relatively small registration error. In an embodiment, displacement vectors $\overline{D}(k)$ are determined so that $NRT_1(\bar{x})$ substantially maximizes NMI between image $iRT_1 \cdot ST\text{-}iMRI_o (\bar{x})$ and image $ST\text{-}iMRI_1 (\bar{x}')$.

Maximization of NMI is optionally subject to constraints on at least one or any combination of more than one of $NRT_1(\bar{x})$ and its derivatives. In an embodiment of the disclosure, conditions and constraints that one or any combination of more than one of $NRT_1 (\bar{x})$ and its derivatives may be required to satisfy to provide satisfactory non-rigid registration may be expressed as a requirement that $NRT_1 (\bar{x})$ be configured to substantially minimize a cost function, "$COST(NRT_1, ST\text{-}iMRI_o, ST\text{-}iMRI_1)$". In an embodiment of the disclosure the cost function $COST(NRT_1, ST\text{-}iMRI_o, ST\text{-}iMRI_1)$ is function of the negative of an NMI between image $NRT_1 \cdot iRT_1 \cdot ST\text{-}iMRI_o (\bar{x}')$ and image $ST\text{-}iMRI_1 (\bar{x}')$, and a constraint function "CNSTRNT", which is a function of $NRT_1(\bar{x})$, its first and second derivatives and has a form: $COST(NRT_1 \cdot iRT_1 \cdot ST\text{-}iMRI_o(\bar{x}), ST\text{-}iMRI_1 (\bar{x}')) = -\gamma_1 NMI(NRT_1 \cdot iRT_1 \cdot ST\text{-}iMRI_o(\bar{x}'), ST\text{-}iMRI_1(\bar{x}')) + \gamma_2 CNSTRNT(NRT_1(\bar{x}), \partial NRT_1(\bar{x})/\partial \bar{x}, \partial^2 NRT_1(\bar{x})/\partial \bar{x}^2)$, where $\gamma_1$ and $\gamma_2$ are weighting constants. In an embodiment of the disclosure $(\gamma_1 + \gamma_2) = 1$ and for registration of an MRI image to an iMRI image, for example registration of $MRI_o$ to $iMRI_o$, $\gamma_1 = \gamma_2$. For registration of an iMRI image to an iMRI image, for example, $iMRI_1$ to $iMRI_2 \gamma_1 = 0.1$. $CNSTRNT(\cdot)$ may be any suitable function that increases in magnitude with increase in any of its arguments.

Optionally, in a block 75, following determination of non-rigid transform $NRT_1(\bar{x})$, the non-rigid transform is applied to produce a high quality MRI image, $hiQ\text{-}ST\text{-}iMRI_1$, in accordance with an expression $hiQ\text{-}ST\text{-}iMRI_1 = NRT_1 \cdot iRT_1 \cdot iRT_o \cdot ST\text{-}MRI_o$. In an embodiment of the disclosure $hiQ\text{-}ST\text{-}iMRI_1$ is used, optionally in a block 77, to determine a fine tuning transform $FTT_1$ that operates to register high resolution $iRT_o \cdot ST\text{-}MRI_o$ masked to the FOV of the iMRI scanner to $hiQ\text{-}ST\text{-}iMRI_1$ in accordance with an expression $ST\text{-}iMRI_1 \Leftarrow FTT_1 \cdot NRT_1 \cdot iRT_1 \cdot iRT_o \cdot ST\text{-}MRI_o$. Transform $FTT_1$ may comprise a rigid transform and a non-rigid transform, and may be configured to provide a substantially accurate registration between $ST\text{-}iMRI_1$ and $iRT_o \cdot ST\text{-}MRI_o$ using any methods and functions suitable for substantially optimizing $FTT_1$.

For example $FTT_1$ may be configured using cubic B-splines and substantially optimized similarly to the way $NRT_1(\overline{x})$ is configured and substantially optimized as described above. In a block 81 $FTT_1$ is optionally applied to $\cdot NRT_1 \cdot iRT_1 \cdot iRT_o \cdot ST\text{-}MRI_o$ to generate a fine tuned image hiQ-ST-iMRI$_{1*}$=FTT$_1 \cdot$NRT$_1 \cdot$iRT$_1 \cdot$iRT$_o \cdot$ST-MRI$_o$. And in a block 83, optionally, hiQ-ST-iMRI$_{1*}$ is displayed on a suitable video screen or via an augmented reality system, for use in monitoring and directing the open brain medical procedure performed on patient 102.

Resection of brain tissue and lesion tissue in lesion tissue region $LT_o$ segmented in block 22 is optionally performed in a block 85, and in a block 87 a first post resection iMRI image, iMRI$_2$, is optionally acquired. In a block 89 a rigid transform iRT$_2$ that transforms pre-resection image iMRI$_1$ to post-resection iMRI$_2$ may be determined optionally in a manner similar to the way in which rigid transform iRT$_1$ that transforms iMRI$_o$ to iMRI$_1$ is determined, and in accordance with an equation iMRI$_2 \Leftarrow$iRT$_2 \cdot$iMRI$_1$. Whereas the equation iMRI$_2 \Leftarrow$ iRT$_2 \cdot$iMRI$_1$ indicates that rigid transform iRT2 is determined from images that do not have skull tissue voxels removed, optionally iRT$_2$ may be determined after skull tissue voxels are removed and in accordance with an equation ST-iMRI$_2 \Leftarrow$iRT$_2 \cdot$ST-iMRI$_1$. In a block 91, skull tissue voxels may be removed from iMRI$_2$ to provide a soft tissue image of the brain ST-iMRI$_2$ and in a block 93 a non-rigid transform NRT$_2$ may be determined in accordance with an equation ST-iMRI$_2 \Leftarrow$NRT$_2 \cdot$iRT$_2 \cdot$ST-iMRI$_1$.

In a block 95 a fine tuning rigid transform iRT2* is determined in accordance with an equation ST-iMRI$_2 \Leftarrow$iRT2*$\cdot$NRT$_2 \cdot$iRT$_2 \cdot$FTT$_1 \cdot$NRT$_1 \cdot$iRT$_1 \cdot$iRT$_o \cdot$ST-MRI$_o$, where as defined above, FTT$_1$=iRT$_{1*} \cdot$NRT$_{1*}$. In determining iRT2* image ST-iMRI$_2$ may be resampled to voxel sizes substantially the same as voxel sizes in image ST-MRI$_o$ and, optionally, image ST-MRI$_o$ is processed to match a gray level histogram of the image to a gray level histogram of image ST-iMRI$_2$.

Optionally in blocks 97 and 99, image iRT2*$\cdot$NRT$_2 \cdot$iRT$_2 \cdot$FTT$_1 \cdot$NRT$_1 \cdot$iRT$_1 \cdot$ST-iMRI$_1$, which may be written as image iRT2*$\cdot$NRT$_2 \cdot$iRT$_2 \cdot$hiQ-ST-iMRI$_{1*}$ remembering that hiQ-ST-iMRI$_{1*}$=FTT$_1 \cdot$NRT$_1 \cdot$iRT$_1 \cdot$ST-iMRI$_1$, is compared to image ST-iMRI$_2$ to provide an estimate of tissue voxels that appear in pre-resection image ST-iMRI$_1$ and have been removed by resection and are not present in post-resection image ST-iMRI$_2$. To provide the estimate, optionally in block 97, a filtered absolute difference mask, (FADIM) is determined responsive to gray values in image ST-iMRI$_2$ and image iRT2*$\cdot$NRT$_2 \cdot$iRT$_2 \cdot$hiQ-ST-iMRI$_{1*}$.

Let three dimensional spatial location of voxels in image ST-iMRI$_2$ and in image iRT2*$\cdot$NRT$_2 \cdot$iRT$_2 \cdot$hiQ-ST-iMRI$_{1*}$ be indicated by indices i,j,k, and their respective gray levels by ST-iMRI$_2$(i,j,k) and iRT2*$\cdot$NRT$_2 \cdot$iRT$_2 \cdot$hiQ-ST-iMRI$_{1*}$(i,j,k). In an embodiment of the disclosure, FADIM comprises voxels FADIM(i,j,k) at locations (i,j,k). A voxel FADIM(i,j,k) has a value optionally equal to 1 if an absolute difference, |ST-iMRI$_2$(i,j,k)–RT$_{2*} \cdot$NRT$_2 \cdot$iRT$_2 \cdot$hiQ-ST-iMRI$_{1*}$(i,j,k)|, is greater than a threshold α. Otherwise, optionally, the voxel has a value 0. Voxels FADIM(i,j,k) having value 1 define a region of tissue voxels in image iRT2*$\cdot$NRT$_2 \cdot$iRT$_2 \cdot$hiQ-ST-iMRI$_{1*}$ that are candidates for imaging tissue that was removed from the brain of patient 102 by the resection referred to in block 85 performed between the times at which images iMRI$_1$ and iMRI$_2$ were acquired.

In a block 99, algorithm 20 defines regions A and B in image iRT2*$\cdot$NRT$_2 \cdot$iRT$_2 \cdot$hiQ-ST-iMRI$_{1*}$. Region A is a volume of tissue in iRT$_{2*} \cdot$NRT$_2 \cdot$iRT$_2 \cdot$hiQ-ST-iMRI$_{1*}$ defined by a largest 3D connected component of (FADIM)(i,j,k) that has at least one voxel connected to TSF$\cdot$LT$_o$, where TSF$\cdot$LT$_o$ is the volume lesion tissue LT$_o$ (block 22) after transformation by transform iRT2*$\cdot$NRT$_2 \cdot$iRT$_2 \cdot$FTT$_1 \cdot$NRT$_1 \cdot$iRT$_1 \cdot$iRT$_o$. Connected components used in defining region A, may be 4 or 8 neighbor connected components (18 or 26 in 3D??). Region B is a volume of tissue imaged in image iRT$_{2*} \cdot$NRT$_2 \cdot$iRT$_2 \cdot$hiQ-ST-iMRI$_{1*}$ defined by voxels that are in TSF$\cdot$LT$_o$ but not the difference mask FADIM.

In an embodiment of the disclosure, voxels in region A of image iRT2*$\cdot$NRT$_2 \cdot$iRT$_2 \cdot$hiQ-ST-iMRI$_{1*}$ are considered to have exhibited a sufficiently large absolute difference, |ST-iMRI$_2$(i,j,k)–RT$_{2*} \cdot$NRT$_2 \cdot$iRT$_2 \cdot$hiQ-ST-iMRI$_{1*}$(i,j,k)| to represent voxels in image iRT2*$\cdot$NRT$_2 \cdot$iRT$_2 \cdot$hiQ-ST-iMRI$_{1*}$(i,j,k) that have been removed by resection. Therefore in a block 101, in an embodiment, voxels RT$_{2*} \cdot$NRT$_2 \cdot$iRT$_2 \cdot$hiQ-ST-iMRI$_{1*}$(i,j,k) in region A are assigned gray values equal to the gray values of corresponding voxels ST-iMRI$_2$(i,j,k) respectively.

Voxels in region B of image iRT$_{2*} \cdot$NRT$_2 \cdot$iRT$_2 \cdot$hiQ-ST-iMRI$_{1*}$ on the other hand are considered in an embodiment not to have exhibited an absolute difference sufficiently large to warrant them being considered as imaging tissue removed by resection. The absolute difference smaller than a may be assumed to indicate that they image lesion tissue not as yet resected, or healthy brain tissue that has migrated into regions of the brain previously occupied by resected tissue. Region B may be considered in accordance with an embodiment of the specification to be a transition region between resected portions of the brain and non-lesion tissue. In a block 103 therefore, voxels in region B are optionally assigned a gray value that is a linear combination of their own gray value and a gray value of a corresponding voxel in image ST-iMRI$_2$(i,j,k). The replacement gray value may be given by an expression $\lambda_1$ST-iMRI$_2$(i,j,k)+$\lambda_2$RT$_{2*} \cdot$NRT$_2 \cdot$iRT$_2 \cdot$hiQ-ST-iMRI$_{1*}$(i,j,k), where $\lambda_1$ and $\lambda_2$ are constant coefficients. By way of numerical example, $\lambda_1$ and $\lambda_2$ may assume values 0.75 and 0.25 respectively or 0.5 and 0.5.

Let the operation of replacing gray values in image RT$_{2*} \cdot$NRT$_2 \cdot$iRT$_2 \cdot$hiQ-ST-iMRI$_{1*}$ as described above be referred to as resection masking and be represented as carried out by an operator "MRSC". Then an image MRSC$\cdot$RT$_{2*} \cdot$NRT$_2 \cdot$iRT$_2 \cdot$hiQ-ST-iMRI$_{1*}$ may represent the image resulting from resection masking of image RT$_{2*} \cdot$NRT$_2 \cdot$iRT$_2 \cdot$hiQ-ST-iMRI$_{1*}$. In a block 105, a non-rigid fine tuning transform NRT$_{2*}$ is determined that warps MRSC$\cdot$RT$_{2*} \cdot$NRT$_2 \cdot$iRT$_2 \cdot$hiQ-ST-iMRI$_{1*}$ to ST-iMRI$_2$ optionally similarly to the way in which, for example NRT$_2$ or NRT$_1$ was determined, and in accordance with an expression, ST-iMRI$_2 \Leftarrow$NRT$_{2*} \cdot$MRSC$\cdot$RT$_{2*} \cdot$NRT$_2 \cdot$iRT$_2 \cdot$hiQ-ST-iMRI$_{1*}$.

In an embodiment of the disclosure, in a block 107, NRT$_{2*}$ is applied to generate an image hiQ-ST-iMRI$_{2*}$ in accordance with an expression hiQ-ST-iMRI$_{2*}$=NRT$_{2*} \cdot$MRSC$\cdot$RT$_{2*} \cdot$NRT$_2 \cdot$iRT$_2 \cdot$hiQ-ST-iMRI$_{1*}$, and in a block 109 hiQ-ST-iMRI$_{2*}$ is displayed for use in monitoring and directing the open brain medical procedure performed on patient 102.

It is noted that in an embodiment of the invention MRI$_o$ may comprise any of various high resolution MRI images, such as by way of example, a high spatial resolution anatomical MRI image, a functional, fMRI images, and/or a diffusion tensor MRI (DTI). MRI$_o$ may comprise a high resolution composite MRI image, comprising an overlay of two or more high resolution images, for example, an overlay of two or more images selected from a high spatial resolution anatomical MRI image, a functional, fMRI image, and/or a diffusion tensor MRI (DTI). The high spatial resolution $MRI_o$ image or composite $MRI_o$ image may be transformed, in accordance with an embodiment of the disclosure to provide interoperative images that provide details of tissue undergoing a medical procedure at various stages of the procedure that may not be available in images provided by an iMRI scanner. For example, a composite $MRI_o$ image comprising an overlay of a high resolution anatomical image, a DTI image, and an fMRI image of a patient's brain transformed in accordance with an embodiment of the disclosure may provide details of anatomical features, neural tracts, and blood flow in the brain during an open brain procedure that may be unavailable in images provided by an iMRI scanner.

It is noted that rigid and/or non-rigid transforms determined for a given high resolution $MRI_o$ image may be used for transforming different high resolution $MRI_o$ image to provide high resolution interoperative images in accordance with an embodiment of the disclosure. For example, transforms determined in accordance with an embodiment of the disclosure for transforming a high resolution anatomical MRI image to provide high resolution interoperative anatomical images during brain surgery may be used to transform a DTI image to provide interoperative neural tract images during the surgery. The interoperative anatomical and DTI images may be displayed independently of each other during surgery and/or overlaid to provide a single composite interoperative image.

There is therefore provided in accordance with an embodiment of the invention a method of providing an intraoperative magnetic resonance image of a target site of a patient body at which a medical procedure is performed, the method comprising: acquiring a high resolution preoperative magnetic resonance image (MRI), $MRI_o$, of a first region of the patient comprising the target site, the $MRI_o$ image comprising a plurality of slices $MRI_{o,n}$ having voxels; acquiring a preoperative, $iMRI_o$ image of a second region of the patient comprising the target site, using an iMRI scanner having a field of view (FOV), the $iMRI_o$ image comprising a plurality of slices $iMRI_{o,m}$ having voxels; registering the $MRI_o$ image to the $iMRI_o$ image to provide a rigid body transform ($iRT_o$) that transforms image $MRI_o$ to image $iMRI_o$; acquiring an $iMRI_1$ image of the target site during performance of the medical procedure; registering image $iMRI_o$ to image $iMRI_1$ to determine a non-rigid body transform ($NRT_1$); and applying $iRT_o$ and $NRT_1$ to image $MRI_o$ to provide a high resolution (hiQ-$iMRI_1$) image.

Optionally registering image $MRI_o$ to image $iMRI_o$ comprises determining whether a voxel in the $iMRI_o$ image is a marginal voxel located near an extremity of the FOV, and if the voxel is determined to be marginal, registering the $MRI_o$ image to the $iMRI_o$ image independent of the voxel. Optionally determining whether a voxel is marginal comprises determining an area of an intersection of the FOV with a slice comprised in image $iMRI_o$ that contains the voxel and determining that the voxel is marginal if the area of intersection is less than a threshold area. The method may comprise determining the threshold to be equal to a fraction less than one of a maximum intersection area of a slice of the plurality of slices in image $iMRI_o$ with the FOV. Optionally, the fraction is between about 0.5 and about 0.8.

In an embodiment of the disclosure registering image $MRI_o$ to image $iMRI_o$ image comprises segmenting tissue imaged in voxels comprised in slices of the plurality of slices in image $iMRI_o$ to identify tissues in image $iMRI_o$. The $iMRI_o$ image may comprise voxels imaging a first tissue type located in the target site and voxels imaging a second tissue type located outside of the target site and the method optionally comprises determining at least one connected region of voxels in the image $iMRI_o$ that are identified as candidates for imaging the second tissue type. Optionally, the first tissue comprises brain tissue and the second tissue comprises skull tissue.

Additionally or alternatively, the method may comprise performing a digital Radon transform of a connected region of the determined at least one connected region in each slice in which the connected region appears. The method may comprise determining that the connected region images a particular component of the patient responsive to at least one constraint that is a function of the Radon transform. Optionally, the at least one constraint comprises at least one constraint that is a function of a Radon angle, $\theta_M$, for which an average, $\overline{RM}(\theta_M)$, of maximum values of the Radon transform at each radon angle $\theta$ for slices of the plurality of slices of the $iMRI_o$ in which the connected region appears, is maximum. In an embodiment the at least one constraint comprises at least one or any combination of more than one of a constraint on $\overline{RM}(\theta_M)$, $\overline{\rho}(\theta_M)$, and $\sigma(\theta_M)$, where $\overline{\rho}(\theta_M)$ is an average of Radon distances at Radon angle $\theta_M$ in slices of the plurality of slices in the $iMRI_o$ image in which the connected region appears and $\sigma(\theta_M)$, and is a standard deviation of $\overline{\rho}(\theta_M)$.

In an embodiment the method comprises determining a cropping window for slices of the plurality of slices of the $iMRI_o$ image in which a connected region of the at least one connected region appears, the cropping window for any given slice including substantially all of the at least one connected region that appears in the slice. Optionally, the cropping window is defined by a boundary comprising straight line segments. Optionally, the boundary is a polygon. Optionally, the boundary is a rectangle.

In an embodiment the method comprises cropping slices of the plurality of slices for which a cropping window is determined responsive to their respective cropping windows to generate a cropped $iMRI_o$ image. Optionally, the method comprises positioning the cropping window associated with a slice comprised in $iMRI_o$ on a corresponding slice of the plurality of slices comprised in the $MRI_o$ image, and masking the corresponding slice to the cropping window to generate a masked $MRI_o$ image. Optionally, the method comprises registering the masked $MRI_o$ image to the cropped $iMRI_o$ image to determine a rigid body transform $RT(1)o$ between the $MRI_o$ image and the $iMRI_o$ image.

In an embodiment, the method comprises cropping slices of cropped slices in the cropped $iMRI_o$ image responsive to a boundary defined by the FOV to define an FOV cropped $iMRI_o$ image. Optionally, the method comprises masking the $MRI_o$ image transformed by transform $RT(1)_o$ responsive to the boundary defined by the FOV, to define an FOV masked $MRI_o$ image.

The method may comprise registering the FOV masked $MRI_o$ image to the FOV cropped $iMRI_o$ image to determine a rigid body transform $RT(2)_o$ between the $MRI_o$ image and the $iMRI_o$ image and a transform $RT(2)_o \cdot RT(1)_o$, that transforms $MRI_o$ to $iMRI_o$. Optionally the method comprises masking transformed image $RT(2)_o \cdot RT(1)_o \cdot MRI_o$ responsive to the FOV and registering the masked image $RT(2)_o \cdot RT(1) \cdot MRI_o$ to FOV cropped image $iMRI_o$ to define a rigid transform $RT(3)_o$ that transforms $RT(2)_o \cdot RT(1)_o \cdot MRI_o$ to FOV cropped image $iMRI_o$.

In an embodiment the method comprises iterating masking, transforming, and registering image $MRI_o$ to FOV cropped image $iMRI_o$ j times to define $iRT_o = RT(j)_o \ldots RT(2)_o \cdot RT(1)_o$ where j is determined responsive to a criterion for ending the iteration.

In an embodiment applying $iRT_o$ and $NRT_1$ to $MRI_o$ comprises determining a transform $iRT_1$ that registers image $iMRI_o$ to image $iMRI_1$ and applying a transform $NRT_1 \cdot iRT_1 \cdot iRT_o$ to image $MRI_o$ to generate image hiQ-$iMRI_1 = NRT_1 \cdot iRT_1 \cdot iRT_o \cdot MRI_o$.

Optionally, the method comprises: determining a rigid transform $iRT_{1*}$ that registers image $NRT_1 \cdot iRT1 \cdot iRT_o \cdot MRI_o$ to image $iMRI_1$; determining a non-rigid transform $NRT_{1*}$ that registers image $iRT1^* \cdot NRT_1 \cdot iRT_1 \cdot iRT_o \cdot MRI_o$ to image $iMRI_1$; and generating an image hiQ-$iMRI_{1*} = NRT_{1*} \cdot iRT_{1*} \cdot NRT_1 \cdot iRT_1 \cdot iRT_o \cdot MRI_o = NRT_{1*} \cdot iRT_{1*} \cdot$hiQ-$iMRI_1$. Optionally, the method comprises: using the iMRI scanner to acquire an image $iMRI_2$ of the target site during performance of the medical procedure after acquiring image $iMRI_1$; determining a rigid transform $iRT_2$ that registers image $iMRI_1$ to image $iMRI_2$; determining a non-rigid transform $NRT_2$ that registers image $iRT_2 \cdot iMRI_1$ to image $iMRI_2$; determining a rigid transform $iRT_{2*}$ that registers image $NRT_2 \cdot iRT_2 \cdot NRT_{1*} \cdot iRT_{1*} \cdot NRT_1 \cdot iRT_1 \cdot iRT_o \cdot MRI_o$ to image $iMRI_2$; determining a non-rigid transform $NRT_{2*}$ that registers image $iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$ to image $iMRI_2$; and generating an image hiQ-$iMRI_{1*} = NRT_{2*} \cdot iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$.

Images $MRI_o$, $iMRI_1$, and $iMRI_2$ may comprise voxels imaging a first tissue type located in the target site and voxels imaging a second tissue type located outside of the target site, and the method may comprise determining non-rigid transforms $NRT_1$, $NRT_{1*}$, $NRT_2$, and $NRT_{2*}$, independent of the voxels imaging the second tissue type. The target site may be lesion tissue in the brain to be treated after a portion of the brain is exposed, the second tissue type is skull tissue, and image $iMRI_o$ is acquired prior to craniotomy, image $iMRI_1$ is acquired after craniotomy. Optionally, the lesion tissue comprises tissue to be resected and image $iMRI_1$ is acquired prior to resection and image $iMRI_2$ is acquired after resection.

In an embodiment, determining $NRT_{2*}$ comprises: determining voxels in image $iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$ that are homologous with corresponding voxels in image $iMRI_2$ having gray values indicating that they image regions of the brain from which tissue is resected; substituting gray values of the homologous voxels in image $iRT_{2*} \cdot NRT_2 \cdot iRT2 \cdot NRT_{1*} \cdot iRT_{1*} \cdot NRT_1 \cdot iRT_1 \cdot iRT_o \cdot MRI_o$ with the gray values of the respective corresponding voxels in image $iMRI_2$; and determining $NRT_{2*}$ responsive to image $iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$ having the substituted gray values. Optionally determining $NRT_{2*}$ comprises: determining a lesion tissue region $LT_o$ in image $MRI_o$ comprising tissue to be resected; determining a region TSF-$LT_o$ in image $iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$ that is substantially congruent with an image region $LT_o$ transformed by a transform $TSF = iRT_{2*} \cdot NRT_2 \cdot iRT_2 \cdot NRT_{1*} \cdot iRT_{1*} \cdot NRT_1 \cdot iRT_1 \cdot iRT_o$; determining voxels in region TSF-$LT_o$ that are not homologous with a region in image $iMRI_2$ having gray values indicating that they image regions of the brain from which tissue is resected; replacing gray values of non-homologous voxels in TSF-$LT_o$ with a linear combination of their respective gray values and gray values of homologous voxels in image $iMRI_2$; and determining $NRT_{2*}$ responsive to the replaced gray values.

In an embodiment of the disclosure image $MRI_o$ may comprise at least one of or any combination of at least two of; a high resolution anatomical MRI image; an fMRI image; and/or a DTI image.

There is further provided in accordance with an embodiment of the disclosure apparatus comprising: a high resolution MRI scanner operable to acquire a high resolution $MRI_o$ image of a region of a patient's body that includes a target site of the body at which a medical procedure is performed prior to performance of the procedure; a relatively low resolution iMRI scanner operable to acquire an $iMRI_o$ image prior to performance of the procedure of a region of the patient's body that includes the target site, and at least one iMRI image, $iMRI_n$ of a region of the body that includes the target site during the procedure; and a processor configured to process an iMRI image acquired by the iMRI scanner using a method in accordance with any of the methods in the disclosure.

There is further provided in accordance with an embodiment of the disclosure apparatus comprising: a high resolution MRI scanner operable to acquire a high resolution $MRI_o$ image of a region of a patient's body that includes a target site of the body at which a medical procedure is performed prior to performance of the procedure; a relatively low resolution iMRI scanner operable to acquire an $iMRI_o$ image prior to performance of the procedure of a region of the patient's body that includes the target site, and at least one iMRI image, $iMRI_n$ of a region of the body that includes the target site during the procedure; and a processor configured to:

register image $MRI_o$ to image $iMRI_o$ to determine a rigid body transform $iRT_o$ that transforms $MRI_o$ to $iMRI_o$; register an n-th image, $iMRI_n$, comprising an image of the target site that is acquired by the iMRI scanner during the procedure to an (n+1)-st image $iMRI_{n+1}$ acquired by the iMRI scanner during the procedure to determine rigid and non rigid transforms $iRT_{n+1}$ and $NRT_{n+1}$ respectively that transform image $iMRI_n$ to image iMRI n+1; register image $NRT_{n+1} \cdot iRT_{n+1} \ldots NRT_{1*} \cdot iRT_{1*} \cdot NRT_1 \cdot iRT_1 \cdot iRT_o \cdot MRI_o$ to image $iMRI_{n+1}$ to determine rigid and non-rigid transforms $iRT_{n+1*}$ and $NRT_{n+1*}$ respectively; that transform image $NRT_{n+1} \cdot iRT_{n+1} \ldots NRT_{1*} \cdot iRT_{1*} \cdot NRT_1 \cdot iRT_1 \cdot iRT_o \cdot MRI_o$ to image $iMRI_{n+1}$ and; generate an image hiQ-$iMRI_{1*} = NRT_{n+1*} \cdot iRT_{n+1*} \cdot NRT_{n+1} \cdot iRT_{n+1} \ldots \cdot NRT_{1*} \cdot iRT_{1*} \cdot NRT_1 \cdot iRT_1 \cdot iRT_o \cdot MRI_o$. for use in the procedure.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method of providing an intraoperative magnetic resonance image of a target site of a patient body at which a medical procedure is performed, the method comprising:
acquiring a high resolution preoperative magnetic resonance image (MRI), $MRI_o$, of a first region of the patient comprising the target site, the $MRI_o$ image comprising a plurality of slices $MRI_{o,n}$ having voxels;
acquiring a preoperative, $iMRI_o$ image of a second region of the patient comprising the target site, using an iMRI scanner having a field of view (FOV), the $iMRI_o$ image comprising a plurality of slices $iMRI_{o,m}$ having voxels;
registering the $MRI_o$ image to the $iMRI_o$ image to provide a rigid body transform ($iRT_0$) that transforms image $MRI_o$ to image $iMRI_o$;
acquiring an $iMRI_1$ image of the target site during performance of the medical procedure;
registering image $iMRI_o$ to image $iMRI_1$ to determine a non-rigid body transform ($NRT_1$); and
applying $iRT_0$ and $NRT_1$ to image $MRI_o$ to provide a high resolution (hiQ-$iMRI_1$) image.

2. The method according to any of claim 1 wherein registering image $MRI_o$ to image $iMRI_o$ comprises determining whether a voxel in the $iMRI_o$ image is a marginal voxel located near an extremity of the FOV, and if the voxel is determined to be marginal, registering the $MRI_o$ image to the $iMRI_o$ image independent of the voxel.

3. The method according to claim 2 wherein determining whether a voxel is marginal comprises determining an area of an intersection of the FOV with a slice comprised in image $iMRI_o$ that contains the voxel and determining that the voxel is marginal if the area of intersection is less than a threshold area.

4. The method according to claim 3 and comprising determining the threshold to be equal to a fraction less than one of a maximum intersection area of a slice of the plurality of slices in image $iMRI_o$ with the FOV.

5. The method according to claim 4 wherein the fraction is between about 0.5 and about 0.8.

6. The method according to claim 1 wherein registering image $MRI_o$ to image $iMRI_o$ image comprises segmenting tissue imaged in voxels comprised in slices of the plurality of slices in image $iMRI_o$ to identify tissues in image $iMRI_o$.

7. The method according to claim 6 wherein the $iMRI_o$ image comprises voxels imaging a first tissue type located in the target site and voxels imaging a second tissue type located outside of the target site and comprising determining at least one connected region of voxels in the image $iMRI_o$ that are identified as candidates for imaging the second tissue type.

8. The method according to claim 7 wherein the first tissue comprises brain tissue and the second tissue comprises skull tissue.

9. The method according to claim 7 and comprising performing a digital Radon transform of a connected region of the determined at least one connected region in each slice in which the connected region appears.

10. The method according to claim 9 and comprising determining that the connected region images a particular component of the patient responsive to at least one constraint that is a function of the Radon transform.

11. The method according to claim 10 wherein the at least one constraint comprises at least one constraint that is a function of a Radon angle, $\theta_M$, for which an average, $\overline{RM}(\theta_M)$, of maximum values of the Radon transform at each radon angle $\theta$ for slices of the plurality of slices of the $iMRI_o$ in which the connected region appears, is maximum.

12. The method according to claim 11 wherein the at least one constraint comprises at least one or any combination of more than one of a constraint on $\overline{RM}(\theta_M)$, $\overline{\rho}(\theta_M)$, and $\sigma(\theta_M)$, where $\overline{\rho}(\theta_M)$ is an average of Radon distances at Radon angle $\theta_M$ in slices of the plurality of slices in the $iMRI_o$ image in which the connected region appears and $\sigma(\theta_M)$, and is a standard deviation of $\overline{\rho}(\theta_M)$.

13. The method according to claim 7 and comprising determining a cropping window for slices of the plurality of slices of the $iMRI_o$ image in which a connected region of the at least one connected region appears, the cropping window for any given slice including substantially all of the at least one connected region that appears in the slice.

14. The method according to claim 1 wherein applying $iRT_0$ and $NRT_1$ to $MRI_o$ comprises determining a transform $iRT_1$ that registers image $iMRI_o$ to image $iMRI_1$ and applying a transform $NRT_1 \cdot iRT_1 \cdot iRT_0$ to image $MRI_o$ to generate image hiQ-$iMRI_1$=$NRT_1 \cdot iRT_1 \cdot iRT_o \cdot MRI_o$.

15. The method according to claim 14 and comprising:
determining a rigid transform $iRT_{1*}$ that registers image $NRT_1 \cdot iRT_1 \cdot iRT_o \cdot MRI_o$ to image $iMRI_1$;
determining a non-rigid transform $NRT_{1*}$ that registers image $iRT_{1*} \cdot NRT_1 \cdot iRT_1 \cdot iRT_o \cdot MRI_o$ to image $iMRI_1$; and
generating an image hiQ-$iMRI_{1*}$=$NRT_{1*} \cdot iRT_{1*} \cdot NRT_1 \cdot iRT_1 \cdot iRT_o \cdot MRI_o$=$NRT_{1*} \cdot iRT_{1*} \cdot$hiQ-$iMRI_1$.

16. The method according to claim 15 and comprising:
using the iMRI scanner to acquire an image $iMRI_2$ of the target site during performance of the medical procedure after acquiring image $iMRI_1$;
determining a rigid transform $iRT_2$ that registers image $iMRI_1$ to image $iMRI_2$;
determining a non-rigid transform $NRT_2$ that registers image $iRT_2 \cdot iMRI_1$ to image $iMRI_2$;
determining a rigid transform $iRT_{2*}$ that registers image $NRT_2 \cdot iRT_2 \cdot NRT_{1*} \cdot iRT_{1*} \cdot NRT_1 \cdot iRT_1 \cdot iRT_o \cdot MRI_o$ to image $iMRI_2$;
determining a non-rigid transform $NRT_{2*}$ that registers image
$iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$ to image $iMRI_2$; and
generating an image hiQ-$iMRI_{1*}$=$NRT_{2*} \cdot iRT_{2*} \cdot NRT_2 \cdot iRT_2 \cdot NRT_{1*} \cdot iRT_{1*} \cdot NRT_1 \cdot iRT_1 \cdot iRT_o \cdot MRI_o$.

17. The method according to claim 16 wherein images $MRI_o$, $iMRI_1$, and $iMRI_2$ comprise voxels imaging a first tissue type located in the target site and voxels imaging a second tissue type located outside of the target site, and determining non-rigid transforms $NRT_1$, $NRT_{1*}$, $NRT_2$, and $NRT_{2*}$, independent of the voxels imaging the second tissue type.

18. An apparatus comprising:
a high resolution MRI scanner operable to acquire a high resolution $MRI_o$ image of a region of a patient's body that includes a target site of the body at which a medical procedure is performed prior to performance of the procedure;
a relatively low resolution iMRI scanner operable to acquire an $iMRI_o$ image prior to performance of the procedure of a region of the patient's body that includes the target site, and at least one iMRI image, $iMRI_n$ of a region of the body that includes the target site during the procedure; and
a processor configured to process an iMRI image acquired by the iMRI scanner using a method in accordance with claim 2.

19. An apparatus comprising:

a high resolution MRI scanner operable to acquire a high resolution $MRI_o$ image of a region of a patient's body that includes a target site of the body at which a medical procedure is performed prior to performance of the procedure;

a relatively low resolution iMRI scanner operable to acquire an $iMRI_o$ image prior to performance of the procedure of a region of the patient's body that includes the target site, and at least one iMRI image, $iMRI_n$ of a region of the body that includes the target site during the procedure; and a processor configured to:

register image $MRI_o$ to image $iMRI_o$ to determine a rigid body transform $iRT_0$ that transforms $MRI_o$ to $iMRI_o$;

register an n-th image, $iMRI_n$, comprising an image of the target site that is acquired by the iMRI scanner during the procedure to an (n+1)-st image $iMRI_{n+1}$ acquired by the iMRI scanner during the procedure to determine rigid and non rigid transforms $iRT_{n+1}$ and $NRT_{n+1}$ respectively that transform image $iMRI_n$ to image $iMRI_{n+1}$;

register image $NRT_{n+1} \cdot iRT_{n+1} \cdot \ldots \cdot NRT_{1*} \cdot iRT_{1*} \cdot NRT_1 \cdot iRT_1 \cdot iRT_o \cdot MRI_o$ to image $iMRI_{n+1}$ to determine rigid and non-rigid transforms $iRT_{n+1*}$ and $NRT_{n+1*}$ respectively; that transform image $NRT_{n+1} \cdot iRT_{n+1} \cdot \ldots \cdot NRT_{1*} \cdot iRT_{1*} \cdot NRT_1 \cdot iRT_1 \cdot iRT_o \cdot MRI_o$ to image $iMRI_{n+1}$; and generate an image $hiQ\text{-}iMRI_{1*} = NRT_{n+1*} \cdot iRT_{n+1*} \cdot NRT_{n+1} \cdot iRT_{n+1} \cdot \ldots \cdot NRT_{1*} \cdot iRT_{1*} \cdot NRT_1 \cdot iRT_1 \cdot iRT_o \cdot MRI_o$, for use in the procedure.

* * * * *